US007060874B2

(12) United States Patent
Wilkins

(10) Patent No.: US 7,060,874 B2
(45) Date of Patent: Jun. 13, 2006

(54) BIOENGINEERING COTTON FIBER PROPERTIES

(75) Inventor: Thea A. Wilkins, Woodland, CA (US)

(73) Assignee: The Regents of the University of California, Oakland, CA (US)

( * ) Notice: Subject to any disclaimer, the term of this patent is extended or adjusted under 35 U.S.C. 154(b) by 297 days.

(21) Appl. No.: 10/440,352

(22) Filed: May 16, 2003

(65) Prior Publication Data
US 2004/0006794 A1     Jan. 8, 2004

Related U.S. Application Data

(63) Continuation-in-part of application No. 10/150,559, filed on May 17, 2002, now abandoned.

(51) Int. Cl.
*C12N 15/29* (2006.01)
*C12N 15/82* (2006.01)
*C12N 5/04* (2006.01)
*A01H 5/00* (2006.01)

(52) U.S. Cl. ............... 800/290; 800/298; 800/314; 800/278; 800/260; 800/287; 536/23.1; 536/23.6; 435/468

(58) Field of Classification Search ............... 536/23.1, 536/23.6, 24.1; 800/298, 290, 287, 278, 800/314, 260; 435/468
See application file for complete search history.

(56) References Cited

U.S. PATENT DOCUMENTS

| 4,801,540 A | 1/1989 | Hiatt et al. |
| 5,034,323 A | 7/1991 | Jorgensen et al. |
| 5,231,020 A | 7/1993 | Jorgensen et al. |
| 5,283,184 A | 2/1994 | Jorgensen et al. |
| 5,495,070 A | 2/1996 | John et al. |
| 5,589,583 A | 12/1996 | Klee et al. |
| 5,597,718 A | 1/1997 | John et al. |
| 5,602,321 A | 2/1997 | John |
| 5,608,148 A | 3/1997 | John |
| 5,880,330 A | 3/1999 | Weigel et al. |

OTHER PUBLICATIONS

Bowie et al, Science 247:1306-1310, 1990.*
McConnell et al, Nature 411 (6838):709-713, 2001.*
Vodjani, F. et al.; NCBI database for nucleotide sequences, National Center for Biotechnology Information, National Library of Medicine, NIH (Bethesda, MD USA); 1997, Accession No. AF008939.
Andreo et al., "Higher plant phosphoenolpyruvate carboxylase, Structure and regulation," *FEBS Letters*, 213(1):1-8 (1987).
Blume, "Expression of ACC oxidase promoter-GUS fusions in tomato and *Nicotiana plumbaginifolia* regulated by developmental and environmental stimuli," *Plant J.*, 12(4):731-746 (1997).

Busk, "Regulatory elements *in vivo* in the promoter of the abscisic acid responsive gene *rab17* from maize," *Plant J.*, 11(6):1285-1295 (1997).
Chollet et al., "Phosphoenolpyruvate Carboxylase: A Ubiquitous, Highly Regulated Enzyme in Plants," *Annu. Rev. Plant Mol. Biol.*, 47:273-298 (1996).
Cole-Strauss et al., "Correction of the Mutation Responsible for Sickle Cell Anemia by an RNA-DNA Oligonuclotide," *Science*, 273:1386-1389 (1996).
Delisle et al., "Transcriptional Control of Alcohol Dehydrogenase Genes in Plants," *Int. Rev. Cytol.*, 123:39-60 (1990).
Ficker et al., "A promoter directing high level expression in pistils of transgenic plants," *Plant Mol. Biol.*, 35:425-431 (1997).
Gowda et al., "Identification of Promoter Sequences for the Major RNA Transcripts of Figwort Mosaic and Peanut Chlortic Streak Viruses (Caulimovirus Group)," *J. Cell Biochem.*, 13D:301, Abstract No. M 318.
Grewal et al., "A Recombinationally Repressed Region Between *mat2* and *mat3* Loci Shares Homology to Centromeric Repeats and Regulates Directionality of Mating-Type Switching in Fission Yeast," *Genetics*, 146:1221-1238 (1997).
Guerrero, "Promoter sequences from a maize pollen-specific gene direct tissue-specific transcription in tobacco," *Mol. Gen. Genet.*, 224:161-168 (1990).
Hayashi et al., "Activation of a plant Gene by T-DNA Tagging: Auxin-Independent Growth in Vitro," *Science*, 258:1350-1353 (1992).
Huang et al., "The *Arabidopsis ACT11* actin gene is strongly expressed in tissues of the emerging inflorescence, pollen, and developing ovules," *Plant Mol. Biol.*, 33:125-139 (1996).
Jiao et al., "Isolation and sequence of an active-site peptide from maize leaf phosphoenolpyruvate carboxylase inactivated," *Biochimica et Biophysica Acta.*, 1041:291-295 (1990).

(Continued)

*Primary Examiner*—David T. Fox
*Assistant Examiner*—Stuart F. Baum
(74) *Attorney, Agent, or Firm*—Townsend & Townsend and Crew LLP

(57) ABSTRACT

The present invention provides plant fiber expansion (FE) genes that encode FE polypeptides, such as phosphoenol pyruvate carboxylase (PEPcase), expansin, endoglucanase, xyloglucan endoglycosyltransferase (XET), and pectin methyl esterase (PME). The invention further provides fiber-specific promoters. Still further, the invention provides molecular strategies for modulating fiber quality and yield in fiber producing plants by modulating expression of FE genes or mutant forms of FE genes.

20 Claims, 8 Drawing Sheets

OTHER PUBLICATIONS

John, "Gene expression in cotton (*Gossypium hirsutum* L.) fiber: Cloning of the mRNSs," *PNAS*, 89:5769-5773 (1997).

Kempin et al., "Targeted disruption in *Arabidopsis*," *Nature*. 389:802-803 (1997).

Lepiniec et al., "Phosphoenolpyruvate carboxylase: structure, regulation and evolution," *Plant Science*. 99:111-124 (1994).

Ma et al., "Cloning and characterization of a cotton lipid transfer protein gene specifically expressed in fiber cells[1]," *Biochem. Biophys. Acta*, 1344:111-114 (1997).

Manjunath et al., "Molecular characterization and promoter analysis of the maize cytosolic glyceraldehydes 3-phosphate dehydrogenase gene family and its expression during anoxia," *Plant Mol. Biol.*, 33:97-112 (1997).

Martinez et al., "Structure, Evolution and Anaerobic Regulation of a Nuclear Gene Encoding Cytosolic Glyceraldehyde-3-phosphate Dehydrogenase from Maize," *J. Mol. Biol.*, 208:551-565 (1989).

Mett et al., "Copper-controllable gene expression system for whole plants," *PNAS*, 90:4567-4571 (1993).

Mizukami et al., "Functional Domains of the Floral regulator AGAMOUS: Characterization of the DNA Binding Domain and Analysis of Dominant Negative Mutations," *Plant Cell*, 8(8):831-845 (1996).

Mountford et al., "Dicistronic targeting constructs: Reporters and modifiers of mammalian gene expression," *PNAS*, 91:4303-4307 (1994).

Napoli et al., "Introduction of a Chimeric Chalcone synthase Gene into Petunia Results in Reversible Co-Suppression of Homologous Genes in trans," *The Plant Cell*, 2:279-289 (1990).

Offringa et al., "Nonreciprocal homologous recombination between *Agrobacterium* transferred DNA and a plant chromosomal locus," *PNAS*, 90:7346-7350 (1993).

Orford et al., "Specific expression of an expansin gene during elongation of cotton fibres," *Biochem. Biophys. Acta.*, 1398(3):342-346 (1998).

Pathirana et al., "Alfalfa root nodule phosphoenolpyruvate carboxylase: characterization of the cDNA and expression in effective and plant-controlled ineffective nodules," *Plant Mol. Biol.*, 20:437-450 (1992).

Puchta et al., "Homologous recombination in plants," *Experientia*. 50:277-284 (1994).

Reiser, "The *Belli* Gene Encoldes a Homeodomain Protein Involved in Pattern Formation in the Arabidopsis Ovule Primordium," *Cell*. 83:735-742 (1995).

Rinehart, "Tissue-specific and Developmental Regulation of Cotton Gene $FbL2A^1$," *Plant Physiol.*, 112:1131-1141 (1996).

Schena et al., "A steroid-inducible gene expression system for plant cells," *PNAS*, 88:10421-10425 (1991).

Sheehy et al., "Reduction pf polygalacturonase activity in tomato fruit by antisense RNA," *PNAS*. 85:8805-8809 (1988).

Shimizu et al., "Changes in Levels of mRNAs for Cell Wall-Related Enzymes in Growing Cotton Fiber Cells[1]," *Plant Cell Physiol.*, 38:375-378 (1997).

Slocombe et al., "Temporal and Tissue-Specific Regulation of a *Brassica napus* Stearoyl-Acyl Carrier Protein Desaturase Gene[1]," *Plant Physiol.*, 104:1167-1176 (1994).

Swoboda et al., "Intrachromosomal homologous recombination in whole plants," *Embo J.*, 13(2):484-489 (1994).

Tiwari et al., "Cotton (*Gossypium hirsutum*) seed trichomes expand via diffuse growing mechanism," *Can. J. Bot.*, 73:746-757 (1995).

Vaulont et al., "Disruption of the adenosine deaminase (ADA) gene using a dicistronic promoterless construct: production of an ADA-deficient homozygote ES cell line," *Transgenic Res.*, 4:247-255 (1995).

Weising et al. "Foreign Genes in Plants: Transfer, Structure, Expression, and Applications" *Ann. Rev. Genetics*. 22:421-477 (1988).

Xu et al., "Targeted disruption of *ATM* leads to growth retardation, chromosomal fragmentation during meiosis, immune defects and thymic lymphoma," *Genes Dev.*, 10:2411-2422 (1996).

Yoon et al., "Targeted gene correction of episomal DNA in mammalian cells mediated by a chimeric RNA-DNA oligonucleotide," *PNAS*, 93:2071-2076 (1996).

Zhong et al., "The circadian clock gates expression of two *Arabidopsis* catalase genes to distinct and opposite circadian phases," *Mol. Gen. Genet.*, 251:196-203 (1996).

\* cited by examiner

```
TTTCACTTTCTGGTGTTCAGTCATAAGTTACCCATTATTTTATCTGTTTTTCTAGCGATTTCTTGGT
GTGGGGCATCACGGAATTCACTTCCAAAGAGATAGGATTTGATTCATCTTTTGTTTTCCGGGTTT
GGGTTTGGGTTCGGCGGATTCTTCGCCACAAATTATTTTTATCCTTTTACACCGCAAAATAATAA
ATTTCATCCGTAATTGTTCCTTTCTTTTTCCTGCCTTTCATTGGTTCATAATTTAAAGTTTTGGCTT
TGGTAGTCAAGTAAAAAGACAGAGATGGCAGGTAGAAAAGTAGAGAAGATGGCTTCAATAGAT
GCACAACTAAGGCTATTAGCACCTGGGAAAGTCTCTGAGGATGATAAGTTGGTTGAATATGATG
CTGTGCTACTGGATCGTTTTCTTGATATTCTTCAGGATTTGCATGGAGAGGATATCAGAGAAACG
GTTCAAGAATGCTACGAGCTTTCTGCGGAGTACGAAGGAAAGCATGATCCTAAAATATTGGAGG
AGCTTGGCAAGGTACTTACAAGCTTGGATCCTGGGGACTCAATTGTTGTTACCAAATCATTTTCC
CACATGCTTAACTTGGGAAACTTGGCCGAGGAGGTTCAAATTGCATATAGACGAAGGATTAAGT
TGAAGAAAGGAGATTTTGCTGATGAGAGTTCAGCAACAACTGAATCAGATATTGAAGAGACGTT
CAAGCGACTTGTGGGGCAGTTGAACAAGTCCCCTGAAGAAGTTTTTGATGCTTTGAAGAATCAG
ACTGTAGATTTAGTCTTAACTGCACATCCTACACAGTCTGTTCGAAGATCTTTACTTCAAAAACA
CGGAAGGATACGTAATTGTTTGACACAATTGTATGCTAAAGACATTACACCTGATGATAAGCAG
GAACTTGATGAGGCACTACAAAGGGAGATTCAAGCTGCTTTTCGCACAGATGAGATCCGAAGGA
ATCCTCCCACCCCACAAGATGAGATGAGAGCAGGAATGAGCTACTTCCACGAGACAATCTGGAA
AGGTGTACCAAAATTCTTGCGTCGTGTTGACACAGCTTTGAAGAACATAGGGATAAATGAACGT
GTTCCATACAATGCCCCTCTTATTCAATTCTCTTCATGGATGGGAGGGATCGTGATGGAAACCC
CAGGGTAACTCCTGAAGTTACAAGAGATGTCTGCTTATTAGCTAGAATGATGGCTGCTAACTTGT
ACTTCTCCCAAATAGAGGATCTTATGTTTGAGTTATCAATGTGGCGTTGCAGCGATGAACTTCGT
ATTCGTGCAGATGAACTCCATAGGTCCTCCAAAAAGGATGCAAAGCATTACATAGAATTTTGGA
AACAGATTCCTCCAAATGAGCCATATCGCATTATTCTTGGTGATGTGAGGGACAAGCTGTATAAT
ACACGTGAACGTGCTCGTAGCCTGTTGGCCAATGGATTTTCTGACATTCCTGAAGAAGCAGCATT
TACCAATGTGGAGCAGTTTCTGGAGCCTCTTGAACTCTGCTATAGATCACTCTGTGCTTGTGGTG
ATCGGCCAATAGCTGATGGAAGCCTTCTTGATTTCTTACGGCAAGTTTCTACCTTTGGGCTTTCAC
TTGTGAGGCTTGATATCCGACAGGAATCTGATAGACATACTGATGTCCTTGATGCTATCACAAAG
CACCTGGATATTGGATCTTATCGAGAATGGCCTGAGGAACGCCGACAGGAATGGCTCTTATCTG
AACTCAGAGGCAAGCGCCCTCTATTCGGCCCTGATCTTCCCAAAACAGAAGAAGTCGCTGATGT
ATTGGACACATTTCATGTCATTTCTGAACTGCCTTCAGACAGCTTTGGTGCCTATATAATCTCAAT
GGCTACAGCCCCATCTGATGTGCTTGCTGTTGAGCTTTTACAACGTGAATGCCATGTAAAGCAAC
CATTACGGGTAGTTCCATTGTTTGAAAAACTCGCTGATCTTGAAGCTGCTCCTGCTGCTGTGGCTC
GTCTCTTCTCTATAGATTGGTACAGAGACCGGATCAATGGGAAACAGGAAGTGATGATAGGTTA
TTCAGATTCAGGAAAGGATGCTGGCCGTCTTTCTGCAGCATGGCAGCTATACAAGGCTCAGGAG
GAACTTGTAAAGGTGGCAAAGCAGTATGGTGTTAAGCTTACAATGTTCCATGGCCGAGGAGGGA
CAGTTGGAAGAGGAGGGGGACCCACGCATCTTGCTATATTGTCTCAACCACCCGATACAATTCAT
GGATCACTTCGTGTAACAGTTCAAGGTGAAGTTATTGAACAATCATTTGGAGAGGAGCACTTGTG
CTTCAGGACGCTTCAACGTTTTACTGCTGCTACACTTGAGCATGGAATGCATCCCCCTGTCTCACC
AAATCCAGAATGGCGTGCACTCATGGATGAAATGGCAGTAGTTGCAACAAAGGAATACCGTTCT
GTAGTCTTCCAGGAACCTCGCTTTGTTGAATACTTCCGCCTAGCAACACCAGAATTGGAGTATGG
TCGGATGAATATTGGAAGCCGTCCATCAAAAAGGAAACCAAGTGGAGGCATTGAATCACTCCGT
GCAATCCCATGGATCTTTGCATGGACTCAAACAAGATTTCATTTACCTGTGTGGCTTGGCTTTGG
GGCTGCATTTAAGCACGTCATTCAGAAGGATATAAAGAATCTCCACATGCTCCAGGAGATGCAC
AACCAATGGCCTTTCTTTAGGGTCACAATGGACTTAATTGAAATGGTATTTGCCAAGGGAGACCC
TGGAATCGCTGCCTTATATGACAAGCTGCTAGTGTCAAAGGAACTCTGGCCCTTTGGAGAGAACT
TGAGAGCTAACTATGAAGACACTAAACGACTTGTTCTCCAGGTTGCTGGACACAGAGATCTTCTT
GAAGGTGACCCTTACCTGAAGCAGAGGCTCCGACTTCGTGATGCTTACATCACAACCCTTAATGT
GTGCCAAGCGTACACTTTGAAAAGGATCCGTGACCCTGATTATCATGTCAAGGTCAGGCCTCACT
TATCCAGGGAATACATGGAATCAAGCAAGGCGGCAGCTGAGCTTGTGAAACTTAACCCTACAAG
CGAGTATGCTCCTGGTCTGGAAGACACCCTTATTTTGACCATGAAGGGTATTGCTGCTGGAATGC
AAAACACTGGTTAAAACTTGCGGATTGTTGTTTCCTTGTGTTGTTATGCTCCTTAGTTTATTTTTA
ATGGATGTTGCTTTGCGTCAAGTAAACCTTTTATATTACTATTATTATCGGTTGGGTTAATTTCAT
ATTTGGCTCATATATTACTAAGTGTTGTCAGTCTGGTATCTCTATAATAATACATATTAACATGAT
TTCCCATTCAAAAAAAAAAAAAAAAAAAAAAAAAAA
```

FIGURE 1

AGRKVEKMASIDAQLRLLAPGKVSEDDKLVEYDAVLLDRFLDILQDLHGEDIRETVQECYELSAE
YEGKHDPKILEELGKVLTSLDPGDSIVVTKSFSHMLNLGNLAEEVQIAYRRRIKLKKGDFADESSA
TTESDIEETFKRLVGQLNKSPEEVFDALKNQTVDLVLTAHPTQSVRRSLLQKHGRIRNCLTQLYAK
DITPDDKQELDEALQREIQAAFRTDEIRRNPPTPQDEMRAGMSYFHETIWKGVPKFLRRVDTALK
NIGINERVPYNAPLIQFSSWMGGDRDGNPRVTPEVTRDVCLLARMMAANLYFSQIEDLMFELSM
WRCSDELRIRADELHRSSKKDAKHYIEFWKQIPPNEPYRIILGDVRDKLYNTRERARSLLANGFSDI
PEEAAFTNVEQFLEPLELCYRSLCACGDRPIADGSLLDFLRQVSTFGLSLVRLDIRQESDRHTDVLD
AITKHLDIGSYREWPEERRQEWLLSELRGKRPLFGPDLPKTEEVADVLDTFHVISELPSDSFGAYIIS
MATAPSDVLAVELLQRECHVKQPLRVVPLFEKLADLEAAPAAVARLFSIDWYRDRINGKQEVMI
GYSDSGKDAGRLSAAWQLYKAQEELVKVAKQYGVKLTMFHGRGGTVGRGGGPTHLAILSQPPD
TIHGSLRVTVQGEVIEQSFGEEHLCFRTLQRFTAATLEHGMHPPVSPNPEWRALMDEMAVVATKE
YRSVVFQEPRFVEYFRLATPELEYGRMNIGSRPSKRKPSGGIESLRAIPWIFAWTQTRFHLPVWLGF
GAAFKHVIQKDIKNLHMLQEMHNQWPFFRVTMDLIEMVFAKGDPGIAALYDKLLVSKELWPFGE
NLRANYEDTKRLVLQVAGHRDLLEGDPYLKQRLRLRDAYITTLNVCQAYTLKRIRDPDYHVK
VRPHLSREYMESSKAAAELVKLNPTSEYAPGLEDTLILTMKGIAAGMQNTG

FIGURE 2

GGCACGAGGGTCAGCCAATTGTTTGAGCTAGCTAGCTCTTACTCAAATGGCAACC
AAAACGATGATGTTGCAAATATTTTCACTTTTCTTCTTTTTGTTCAGTATCTGCAA
CTCCATTTTCCTTGGTGCTAATGGAGATGACAATGGTGGTTGGCAAACTGCCCAT
GCCACCTTCTACGGTGGTGCTGATGCTACCGGCACAATGGGGGGAGCTTGTGGTT
ATGGAAACCTGTACAGTCAAGGGTATGGAACGAGCACAGCAGCTTTGAGCACTG
CACTTTTCAACAATGGCTTGAGCTGCGGTGCCTTCTACGAGCTCCGGTGCAACAA
TGATCCTCAATGGTGCATTAGTCGAACCATAACCGTGACAGCCACCAACTTTTGT
CCCCCTAACTATGCTTTATCTAGTGACAATGGCGGGTGGTGCAATCCCCCACGAG
AACACTTTGATTTGGCCGAACCGGCATTCTTGCAGATCGCGGAATATCGAGCTGG
GATCGTCCCTGTTATGTTCAGAAGGGTGTCATGTGTGAAGAAGGAGGCATCAG
GTACACCATGAATGGACATTCGTACTTCAACATGGTGTTGATAACCAACGTGGGA
GGGGCAGGGGATATAACGTCAGTGTCCATCAAGGGTTCCAAAACAGGATGGCTA
CCTATGTCCAGAAATTGGGGCCAAAACTGGCAGAGCAATGCTTACCTTAACGGC
CAAAGCCTCTCTTTCAAAGTGACTGCCAGCGATAGCAGGACTATCACAAACTACA
ATGTAGTGCCCGCTGGTTGGCAATTCGGACAAACTTTTGAAGGAGGCCAGTTTTA
AGACAATATTATAGTGTCCGTCTAATATTAAAACTGGAATTGACATATTACTTAT
ATAAGGCACATGAGCGTTTTATGCCGAGGTAGCAAAGTGGCGCCCGCTGGCTTTA
TGTGTGAAATAGGCGAGCAAGTGCCATTAGCCTATAATATACACATTTCCTATAG
TGAACCAAACTATTAAGTTTGAACTCTAGAAGTGATATCCATAATGTCTGAAATT
TGATTGTTGATGATTGACCATGATATTTATGGTTTTCATTATTGAAATACTTTTT
ATTATAATTTATAAATAAATGAATCATTTCTTTTACAAAAAAAAAAAAAAAAA

FIGURE 3

MATKTMMLQIFSLFFFLFSICNSIFLGANGDDNGGWQTAHATFYGGADATGTMGGA
CGYGNLYSQGYGTSTAALSTALFNNGLSCGAFYELRCNNDPQWCISRTITVTATNFC
PPNYALSSDNGGWCNPPREHFDLAEPAFLQIAEYRAGIVPVMFRRVSCVKKGGIRYT
MNGHSYFNMVLITNVGGAGDITSVSIKGSKTGWLPMSRNWGQNWQSNAYLNGQSL
SFKVTASDSRTITNYNVVPAGWQFG QTFEGGQF

FIGURE 4

```
GGCACGAGCCACTTTGGAAAACCAATGAAGAAAGCACCACTGCCTACTTATACACA
TTTTATTTATCAAACTCAACTTCCTCTTCGTCTTGGTAGATCAGATCTGTCGGTGCTC
CTGCATTTTCCGCCCACTACTCTTCCAAATCCTCATCATGTACGGCAGAAATCCGTG
GGGAGGTCCCCTGGAGATAAACGCCACTGATTCTGCCACTGACGACGACAGGAGCA
GGAATCTGCAGGACCTGGATAGGGCTGCACTCTCTCGCCCCTTGGACGAGACTCAG
CAAAGCTGGCTGCTTGGCCCCGGGGAGCAAAGAAGAAGAAGAAGTACGTTGATC
TCGGATGTATCATTGTGAGCCGCAAGATCTTTGTATGGACCGTGGGGACCCTGCTAG
TCTCCGCCCTCCTGGCCGGACTCATCACCCTCATCGTCAAGACTGTCCCACGTCATC
ACCACCGCCACTCTCCGCCCGATAACTACACTCTGGCTCTTCACAAGGCGCTCATGT
TCTTTAATGCTCAGCGTTCTGGAAAGCTGCCCAAGCATAATAATGTGTCGTGGAGAG
GGAACTCGGGCCTCCAAGATGGCAAATCCGATCCCTCCGTTTTGATGAAAGATCTG
GTCGGCGGATATTACGATGCTGGAGATGCTATCAAGTTTAACTTTCCTGCATCTTTT
TCAATGACTATGTTGAGCTGGAGTGTCATCGAATACAGTGCTAAATACGAGGCTGC
CGGCGAGCTCAATCATGTTAAAGAGATCATCAAATGGGGTACTGATTATCTTCTGA
AGACCTTCAACAATACTGCTGATACCATTGACAGGATTGCAGCGCAGGTAGGGATA
GGAGATACATCTGGAGGAGTTTCAGCCCCAAATGATCATTATTGCTGGATGCGCCCT
GAGGACATTGATTACCCCGTCCTGTATATGAATGTCATAGTTGCTCCGATCTTGCT
GCTGAAATGGCTGCTGCTTTGGCTTCGGCTTCCATCGTTTTCAAAGACAACAAAGCA
TACTCTCAAAAGCTTGTCCATGGTGCCCGAACACTCTTTAAGTTTGCTAGGGATCAA
AGAGGCAGATATAGTGCTGGTCGTTCTGACCCTGCCCTCTTTTATAATTCCTCAAGT
TACTGGGATGAGTTTGTTTGGGGTGGAGCCTGGTTATACTATGCCACTGGGAATTCA
TCCTATCTTCAGTTAGCTACTCATCCTAAACTTGCCAAGCATGCTGGTGCTTTCTGGG
GTGGCCCAGATTATGGTGTTCTTAGCTGGGATAATAAGCTTGCTGGTGCTCAGGTGC
TTCTGAGCCGATTGAGATTGTTTTGAGTCCTGGGTATCCATATGAGGAAATATTGA
GTACGTTTCATAATCAAACCAGCATAATTATGTGCTCATTCCTTCCGGTTTTCACTAG
CTTTAATAGAACAAAAGGAGGTTTGATTCAGTTAAACCATGGAAGGCCTCAGCCAC
TGCAATACGTAGTCAATGCAGCCTTCTTAGCCGCCCTATATAGTGATTATCTTGATG
CTGCTGATACACCTGGATGGTATTGTGGTCCCAATTTCTATTCAACTGATGTCCTGC
GTGAATTTGCCAAAACCCAGATTGATTATATCCTTGGCAAAAATCCTCGAAAAATG
AGCTATGTTGTGGGCTTTGGTAACCATTATCCAAAGCATGTTCACCATAGAGGGCA
TCTATCCCTAAGAATAAGATCAAATATAACTGTAAAGGGGGATGGAAATGGAGGGA
TACGTCAAAACCAAACCCCAACACACTTGTGGGAGCCATGGTAGCAGGACCTGACA
AGCATGATGGGTTTCGTGATGTTCGCACCAACTACAACTATACGGAGCCAACTCTA
GCAGGCAACGCAGGGTTGGTTGCTGCACTCGTGGCATTGTCTGGTGACAAGGCAAC
CGTGATTGACAAGAATACTATTTTTTCTGCAGTTCCACCAATGTTTCCTACACCACC
ACCACTTCCGGCACCTTGGAAACCATGAAAACGTTTTGATCTTTCTTCTGTCCATGT
GTGACTTACAGTCTGATGATTTTGGAATTAGTTTTGGTACGTAAATGACCTTGGAA
GTGTAAGTAACGCAAAAGGCAAGACAGGAGATGAGTGATATGAGACAACCTGGA
CAAAACTCGTGGTGTTTGGCTGTCAGATTGGAGAGTCAGAGAAGCATTCAAACATT
GATAATTTGTATATGAAGTCTATTTGGATTTTGTGGTATACAGACAGACGGAGTGCA
TGTATGATATTAATGTTGTATTATTTGAAACACACCAATATCCATTGACAATAAATT
TGTGTTTAATTGTTGCAGAAATCTGGCCTTTGCTATTACCAAAAAAAAAAAAAAA
AACTCGAG
```

FIGURE 5

ARATLENQRKHHCLLIHILFIKLNFLFVLVDQICRCSCIFRPLLFQILIMYGRNPWGGPL
EINATDSATDDDRSRNLQDLDRAALSRPLDETQQSWLLGPGEQKKKKKYVDLGCIIV
SRKIFVWTVGTLLVSALLAGLITLIVKTVPRHHHRHSPPDNYTLALHKALMFFNAQR
SGKLPKHNNVSWRGNSGLQDGKSDPSVLMKDLVGGYYDAGDAIKFNFPASFSMTM
LSWSVIEYSAKYEAAGELNHVKEIIKWGTDYLLKTFNNTADTIDRIAAQVGIGDTSG
GVSAPNDHYCWMRPEDIDYPRPVYECHSCSDLAAEMAAALASASIVFKDNKAYSQK
LVHGARTLFKFARDQRGRYSAGRSDPALFYNSSSYWDEFVWGGAWLYYATGNSSY
LQLATHPKLAKHAGAFWGGPDYGVLSWDNKLAGAQVLLSRLRLFLSPGYPYEEILS
TFHNQTSIIMCSFLPVFTSFNRTKGGLIQLNHGRPQPLQYVVNAAFLAALYSDYLDAA
DTPGWYCGPNFYSTDVLREFAKTQIDYILGKNPRKMSYVVGFGNHYPKHVHHRGAS
IPKNKIKYNCKGGWKWRDTSKPNPNTLVGAMVAGPDKHDGFRDVRTNYNYTEPTL
AGNAGLVAALVALSGDKATVIDKNTIFSAVPPMFPTPPPLPAPWKPKRFDLSSVHVL
TVFWNFLVRKPWKCKRKKARQEMSDMRQPGQNSWCLAVRLESQRSIQTLIICISLFG
FCGIQTDGVHVYCCIINTPISIDNKFVFNCCRNLAFAITKKKKKKLE

FIGURE 6

CTCAAACCACCTTGTTCTCCCCCCTTCTCCGTCTTTCTGGCAACATGGGTTCACCA
CCACTTTGGGTTCTGCTTCTGGGTGTGTTGTTTATGGCTTCCGGAACAATCGCAGC
TCCCCCTAAGAAGCCTGTAGATGTACCATTCTCCAGAAACTATATGCCTACTTGG
GCTTTTGATCACATTAAGTATTTCAATGGTGGCTCTGACATTCAGCTCCACCTTGA
CAAATACACTGGTACTGGTTTCCAGTCCAAAGGATCATACTTGTTCGGACACTTC
AGTATGCAAATAAAGCTAGTCCCTGGAGATTCTGCTGGGACTGTCACTGCCTGTT
ATTTGTCTTCTCAAAACTCAGAGCATGATGAGATAGATTTTGAGTTCTTGGGCAA
CAGAACAGGGCAACCATACATTCTTCAGACCAATGTGTTCACTGGTGGCAAAGG
AGACAGAGAACAAAGGATTTACCTTTGGTTTGACCCAACCAAAGAATACCACTC
CTACTCTGTCCTCTGGAACATGTATCAGATANTGTTCTTTGTGGACGACATACCA
ATCAGAGTGTTCAAAAACTGCAAAGATTTGGGAGTGAGGTCAAGGGGTGGTCTC
GAAAAGACCGACTGGTCCAAAGCCCCATTCATAGCCGCATACAAGAGCTTCCAC
ATCGACGGGTGCGAGTCGTCGGTGGAAGCCAAGTTCTGCGCCACACAGGGAAAG
CGGTGGTGGGACCAAAAGGCATTCGAGGACCTCGACGCCTATCAGTGGCGCAGA
CTGCGTTGGGTCCGCAACAAGTTCACTATTTACAACTATTGCAGCGATAGGGTGA
GGTACCCCACAATGTCGCCCGAGTGCAAGAGAGACAGAGACGCTTGAGTCATTT
CCATCACCACCGAGTCAATTGCTTGTTGGCCTTCACTTATTTCCACATCAATTTCA
TTATATGTAATTTCACTCCTAAAACATTTGTTTTCGTGATAATATTATTTAAACAT
AGATTACCATCTCTTGACGGGGACAAGACCATNATCTTGTAAGTATAAGTATAA
GAAGCTTGGGATTCGATTTCAAGAAATNNAAGTCTATTTAAAAAAAAAAAAAAA
AAAAACTCGAGGGGGGGCCCGGTACCCAATTCCGCCCTATAGTTGAGTCCTATAC
NATTCCACTGGGCCGTCTTTTACAAC

FIGURE 7

MGSPPLWVLLLGVLFMASGTIAAPPKKPVDVPFSRNYMPTWAFDHIKYFNGGSDIQL

HLDKYTGTGFQSKGSYLFGHFSMQIKLVPGDSAGTVTACYLSSQNSEHDEIDFEFLG

NRTGQPYILQTNVFTGGKGDREQRIYLWFDPTKEYHSYSVLWNMYQIXFFVDDIPIR

VFKNCKDLGVRSRGGLEKTDWSKAPFIAAYKSFHIDGCESSVEAKFCATQGKRWWD

QKAFEDLDAYQWRRLRWVRNKFTIYNYCSDRVRYPTMSPECKRDRDA*VISITTESI

ACWPSLISTSISLYVISLLKHLFS**YYLNIDYHLLTGDKTXIL*V*V*EAWDSISRNXSL

FKKKKKKNSRGGPVPNSAL*LSPIXFHWAVFLQ

FIGURE 8

AAAGCTTTTCTTGGCTCTCTTTGCGTCAATCCTTCTTGTAACTGCCATAGTCACCA
TTGCCACCACCGTCTCCATTTCCAAAAAGAAATCCAGTAATACTGTAGCAGCTCA
CTCCATCATCAAATCTTCATGTAGCTCCACGTTGTACCCAGAGTTATGCTACTCAA
CAATCTCTTCAGCACCAGATGCTGAGACCAAGGTCAAGAACCCCAAGGATGTGA
TTGAATTGTCGTTGAACTTGACGGTGACTGCTGTTCAGAGTAACTATTTGTCCATC
AAAAAGCTCATTAGTACCCGAAGGAAGAGCCTCACGGAGCGCGAAAAGGCTGCC
CTTAACGATTGTCTTGAACTAGTGGATGAGACTTTGGATGAGCTATTCGTAGCTG
AACATGATCTCAGTGACTATCCAAGCTTTAACAAGTCAATTTCCCAACATGCTGA
TGACCTTAAGAGTCTTCTTAGTGCTGCAATGACCAACCAAGAAACTTGCCTTGAT
GGGTTTTCTCACGATAAAGCTGATAAAAAGGTGAGGCAAGCGTTGCTTGACGGG
CAGATGCATGTTTTTCATATGTGTAGTAATGCCCTGGCAATGATCAAGAACTTGA
CGGACACAGACATGGCAAGCCAAGGTTATCATCCATCATCTGGGAGGCAACTTG
AGGAGCAAGACCAAACAGAATGGCCTAAATGGCTGTCGGAGGGAGATAGGAGA
CTGTTACAGGCTACAACAGTGATTCCTAATGTAACAGTGGCCGCTGATGGTAGTG
GAGACTTCCTCACGGTGTCTGAGGCGGTGGCGGCTGCACCGGAGAGAAGCACCA
CGAGGTACATTATTAAGATTAAAGCTGGAGTTTATAGGGAAACGTGGATGTTTCC
AAGTAAGAAAACCAATCTCATGTTTGTGGGAGATGGGAGGGTCAACACCATCAT
CACAGCTAGCAGAAATGTTGTCGATGGCAGCACCACTTTCCACTCTGCCACTGTT
GCTGCGGTAGGGGACGGGTTCTTGGCCAGGGATATAACATTTCAGAACACGGCT
GGACCATCGAAGCACCAAGCAGTGGCACTGCGTGTGGGCTCTGATTTATCAGCAT
TCTACAGGTGTGGCATTTTAGCATACCAGGACACTCTCTATGTCCACAGCCTTCG
CCAATTCTATTCACAATGCCTTGTAGCAGGCAGCGTGGACTTCATATTCGGAAAT
GCAGCAGCAGTGTTGCAAGACTGCGACATTCATGCTCGTCGACCCAATCCAAACC
AAAGGAACATGGTCACCGCACAAGGNCGTAGTGACCCAAACGAGAACACTGGG
ATTGTGATTCANAAATGTNGGATCGGTGCAACCTCGGATTTAGAAGCCGTTAAAT
CCGATTTTGAAACTTATTTAGGGAGACCATGGAAGACACATTCGAAGACTGTTAT
CATGCAATCTGTTATAAGTGATATTATTCATCCTGCTGGTTGGTTCCCATGGGGA
AAAAAAATTCGCACTCNACCTTTGACGTATCNGGAATATCANAATACTNGGCCTG
GANCTTAACNCNTCAANCAGGGTTACATGGAAAAGGGTTATTACNTTATCCCCCA
CATATCCGGAAGCCCAAAACCTACCTGCCTCCGNAATTTTTNTTTGGGGGAACNT
AATTGGGTTTANCCCCNCCGGGNCTTNCCTTTCCCTCNTNGAATCTTTGAAAA

FIGURE 9

XXXXXXXXXKLFLALFASILLVTAIVTIATTVSISKKKSSNTVAAHSIIKSSCSSTLYPE
LCYSTISSAPDAETKVKNPKDVIELSLNLTVTAVQSNYLSIKKLISTRRKSLTEREKAA
LNDCLELVDETLDELFVAEHDLSDYPSFNKSISQHADDLKSLLSAAMTNQETCLDGF
SHDKADKKVRQALLDGQMHVFHMCSNALAMIKNLTDTDMASQGYHPSSGRQLEE
QDQTEWPKWLSEGDRRLLQATTVIPNVTVAADGSGDFLTVSEAVAAAPERSTTRYII
KIKAGVYRETWMFPSKKTNLMFVGDGRVNTIITASRNVVDGSTTFHSATVAAVGDG
FLARDITFQNTAGPSKHQAVALRVGSDLSAFYRCGILAYQDTLYVHSLRQFYSQCLV
AGSVDFIFGNAAAVLQDCDIHARRPNPNQRNMVTAQXRSDPNENTGIVIXKCXIGAT
SDLEAVKSDFETYLGRPWKTHSKTVIMQSVISDIIHPAGWFPWGKKIRTXPLTYXEYX
NTXPGX*XXXQGYMEKGYYXIPHISGSPKPTCLXNFXLGEXNWVXPXRXXPFPXXIF
EX

FIGURE 10

BIOENGINEERING COTTON FIBER PROPERTIES

RELATED APPLICATION INFORMATION

This application is a continuation-in-part of U.S. application Ser. No. 10/150,559 filed May 17, 2002, now abandoned. This application is incorporated by reference herein.

FIELD OF THE INVENTION

The present invention is directed to plant genetic engineering. In particular, it relates to the isolation of nucleic acid molecules that modulate fiber quality and yield, and the use of these nucleic acid molecules to produce transgenic plants with varied cotton fiber characteristics and quality.

BACKGROUND OF THE INVENTION

Cotton is a widely used textile fiber. For example, cotton textiles are used for clothing, home furnishings, blanket fills, toiletry products, industrial garments, etc. The expansive utility of cotton textile products is attributed to the relative ease of cotton production compared to other fibers and their appealing properties. As clothing, cotton fabrics are comfortable to wear because they are soft and breathable. Furthermore, cotton fibers are highly absorptive and possess good wicking properties, thereby allowing the use of the fibers in absorbent articles.

Although cotton is one of the most popular textile fibers used, it has many disadvantages. For example, cotton fabrics become worn out readily after several cycles of laundering. This is because, cotton fibers break or pill due to mechanical agitation during wash and form a lint on the surface of the fabric. In another example, cotton fibers tend to shrink significantly compared to synthetic fibers, even after several cycles of laundry. The shrinkage of cotton textile products, in particular clothing, poses a dilemma for consumers, because the consumers can not readily determine how much their newly purchased cotton clothing will shrink and if the clothing will fit on them to their satisfaction after a few cycles of wash. In yet another example, cotton fabrics tend to wrinkle easily, and require a great deal of care to maintain their shape.

In order to overcome these disadvantages, manufacturers often pre-treat cotton fibers and fabrics. For example, to control lint formation, cotton seeds are delinted prior to a brush delinter, or cotton fabrics are treated with a cellulase solution to remove lint precursors. To reduce wrinkle formation, manufacturers treat cotton fabrics with crosslinking agents, such as formaldehyde. However, these additional processes to treat cotton fibers or fabrics add cost to the manufacture of cotton textile products. Furthermore, chemicals added during the manufacture of cotton fabrics and fibers tend to wash out during laundering and lose their effect over time.

Thus, there is a need to improve the quality of cotton textile products. It would be desirable to avoid using any additives in improving the quality of cotton textile products, because they lose their effect over time, especially after repetitive laundering. Chemical additives may also be toxic to human body. It would also be desirable to reduce any additional processing steps so that the manufacture of cotton textile products will be cost effective. One way to resolve these problems is by improving the quality of cotton fibers themselves, so that the need for additional processing steps is eliminated. Thus, there is a need to improve the cotton fiber characteristics, such as fiber strength, fiber length and fineness.

SUMMARY OF THE INVENTION

The present invention provides isolated nucleic acid molecules comprising a FE polynucleotide sequences. Examples of nucleic acids of the invention include phosphoenol pyruvate carboxylase (PEPcase) sequences at least about 60% identical to SEQ ID NO:1, expansin sequences at least about 60% identical to SEQ ID NO:3, endoglucanase sequences at least about 60% identical to SEQ ID NO: 5, xyloglucan endoglycosyltransferase (XET) sequences at least about 60% identical to SEQ ID NO: 7, and pectin methyl esterase (PME) sequences at least about 60% identical to SEQ ID NO: 9. The isolated nucleic acid molecules of the invention may further comprise a plant promoter operably linked to the FE polynucleotide. The promoter may be, for example, a tissue-specific promoter, in particular, a fiber-specific promoter. The FE polynucleotides may be linked to the promoter in a sense or an antisense orientation.

The invention also provides transgenic plants comprising an expression cassette containing a plant promoter operably linked to a heterologous FE polynucleotide sequence of the invention.

The invention further provides methods of modulating fiber quality in a plant. The methods comprise introducing into the plant an expression cassette containing a plant promoter operably linked to a heterologous FE polynucleotide sequence of the invention. The plant may be any plant and is usually a member of the genus *Gossypium*. In the methods the expression cassette can be introduced into the plant through a sexual cross or using genetic engineering techniques.

The invention also encompasses a method of modulating fiber yield and/or fiber quality in a plant. The method comprises introducing into a plant an expression cassette containing a plant promoter operably linked to a heterologous expansin polynucleotide sequence, which is at least about 80% identical to SEQ ID NO: 3. The heterologous expansin polynucleotide encodes an expansin polypeptide. The heterologous expansin polypeptide may include an amino acid sequence of SEQ ID NO: 4. The heterologous expansin polynucleotide may include a nucleic acid sequence of SEQ ID NO: 3. The method may further contemplate the use of a plant promoter that is an enhanced cotton fiber specific promoter. The plant may be any plant and is usually a member of the genus *Gossypium*.

BRIEF DESCRIPTION OF THE FIGURES.

FIG. 1. Nucleic acid sequence of a PEPCase clone (PEPC1) isolated from a 10 day post-anthesis cotton fiber cDNA library (GenBank Accession Number AF008939) (SEQ ID NO:1).

FIG. 2. Deduced amino acid sequence of the PEPCase clone (PEPC1) isolated from a 10 day post-anthesis cotton fiber cDNA library (GenBank Accession Number AF008939) (SEQ ID NO:2).

FIG. 3. Nucleic acid sequence of an expansin cDNA clone (GhEXP2) (SEQ ID NO:3) isolated from a 10 day post-anthesis cotton fiber *Gossypium hirsutum* cv. Acala SJ-2 ZAPII library.

FIG. 4. Deduced amino acid sequence of the GhEXP2 Expansin protein (SEQ ID NO:4).

FIG. 5. Nucleic acid sequence of a clone encoding the Korrigan homolog from *Arabidopsis,* a member of the EGase family of endo-1,4-beta-D-glucanases isolated from a 10 day post-anthesis cotton fiber *Gossypium hirsutum* cv. *Acala* SJ-2 cDNA library (SEQ ID NO:5).

FIG. 6. Deduced amino acid sequence of the Cotton (*Gossypium hirsutum* L.) 10 dpa Fiber homolog of the *Arabidopsis* Korrigan, a member of the endo-1,4-beta-D-glucanase(EGase)family (SEQ ID NO:6)

FIG. 7. Full length nucleic acid sequence of a xyloglucan endoglycosyltransferase (XET) (SEQ ID NO:7) isolated from a 10 day post-anthesis cotton fiber *Gossypium hirsutum* cv. *Acala* SJ-2 cDNA library.

FIG. 8. Deduced amino acid sequence of the xyloglucan endoglycosyltransferase (XET) (SEQ ID NOS:8, 21, 22, 23 and 24) isolated from a 10 day post-anthesis cotton fiber *Gossypium hirsutum* cv. *Acala* SJ-2 cDNA library.

FIG. 9. Contiguous consensus nucleic acid sequence of the pectin methylesterase (PME) gene assembled from nucleotide sequences 5PME, 3PME, 2PME, and the *Gossypium arboreum* L. cv. AKA8401 *Efiber* EST xgi contig CON_001_18878 (SEQ ID NO:9).

FIG. 10. The deduced protein sequence for a *Gossypium hirsutum* L. fiber pectin methyesterase derived from the PME consensus sequence (SEQ ID NOS:10 and 25).

DEFINITIONS

The phrase "nucleic acid sequence" refers to a single or double-stranded polymer of deoxyribonucleotide or ribonucleotide bases read from the 5' to the 3' end. It includes chromosomal DNA, self-replicating plasmids, infectious polymers of DNA or RNA and DNA or RNA that performs a primarily structural role.

A "promoter" is defined as an array of nucleic acid control sequences that direct transcription of an operably linked nucleic acid. As used herein, a "plant promoter" is a promoter that functions in plants, even though obtained from other organisms, such as plant viruses. Promoters include necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "plant" includes whole plants, plant organs (e.g., leaves, stems, flowers, roots, etc.), seeds and plant cells and progeny of same. The class of plants that can be used in the method of the invention is generally as broad as the class of higher plants amenable to transformation techniques, including angiosperms (monocotyledonous and dicotyledonous plants), as well as gymnosperms. It includes plants of a variety of ploidy levels, including polyploid, diploid, haploid and hemizygous.

A polynucleotide sequence is "heterologous to" an organism or a second polynucleotide sequence if it originates from a foreign species, or, if from the same species, is modified from its original form. For example, a promoter operably linked to a heterologous coding sequence refers to a coding sequence from a species different from that from which the promoter was derived, or, if from the same species, a coding sequence which is different from any naturally occurring allelic variants.

A polynucleotide "exogenous to" an individual plant is a polynucleotide which is introduced into the plant by any means other than by a sexual cross. Examples of means by which this can be accomplished are described below, and include *Agrobacterium*-mediated transformation, biolistic methods, electroporation, and the like. Such a plant containing the exogenous nucleic acid is referred to here as an $R_1$ generation transgenic plant. Transgenic plants that arise from sexual cross or by selfing are descendants of such a plant.

"FE" is an acronym for fiber expansion, and the term is used generically to refer to properties of cotton fibers controlled by the polynucleotides and polypeptides of the present invention. For example, an FE polynucleotide refers to nucleic acids encoding FE polypeptides, such as phosphoenol pyruvate carboxylase (PEPcase), expansin, endoglucanase, xyloglucan endoglycosyltransferase (XET), and pectin methyl esterase (PME).

"Phosphoenol pyruvate carboxylase" or "PEPcase" refers to an enzyme that regulates synthesis of malate. Malate is a primary osmoregulatory solute involved in maintaining cell turgor during fiber expansion. Thus, a "phosphoenol pyruvate carboxylase polynucleotide" or "PEPcase polynucleotide" of the invention is a subsequence or full length polynucleotide sequence of a gene which, when present in a transgenic plant, can be used to modify fiber quality (e.g., fiber length, fiber strength, or fiber fineness) and which is at least about 60%, 70%, 80%, 85%, 90%, 95%, 98% or more identical to SEQ ID NO:1. A PEPcase polynucleotide typically comprises or consists of a coding region of at least about 30–40 nucleotides to about 3400 nucleotides in length. Usually, the nucleic acids are from about 100 to about 500 nucleotides, often from about 500 to about 1500 nucleotides in length or from about 1500 nucleotides in length to about 3400 nucleotides in length.

"Expansin" refers to an enzyme that influences cross-linking relationships in the cell wall and allow cell wall components to "slip" during fiber expansion, thereby allowing the fibers to increase in length. Thus, an "expansin polynucleotide" of the invention is a subsequence or full length polynucleotide sequence of a gene which, when present in a transgenic plant, can be used to modify fiber quality (e.g., fiber length, fiber strength, or fiber fineness) and fiber yield (fiber weight per seed); and which is at least about 60%, 70%, 80%, 85%, 90%, 95%, 98% or more identical to SEQ ID NO:3. An expansin polynucleotide typically comprises or consists of a coding region of at least about 30–40 nucleotides to about 1154 nucleotides in length. Usually, the nucleic acids are from about 100 to about 500 nucleotides, often from about 500 to about 1154 nucleotides in length.

"Endoglucanase" refers to a type of cellulase that cleaves glucan cellulose, thereby controlling the length of cellulose polymers. Thus, an "endoglucanase polynucleotide" of the invention is a subsequence or full length polynucleotide sequence of a gene which, when present in a transgenic plant, can be used to modify fiber quality (e.g., fiber length, fiber strength, or fiber fineness) and which is at least about 60%, 70%, 80%, 85%, 90%, 95%, 98% or more identical to SEQ ID NO:5. An endoglucanase polynucleotide typically comprises or consists of a coding region of at least about 30–40 nucleotides to about 2386 nucleotides in length. Usually, the nucleic acids are from about 100 to about 500 nucleotides, often from about 500 to about 1500 nucleotides in length or from about 1500 nucleotides in length to about 2386 nucleotides in length.

"Xyloglucan endoglycosyltranferase" or "XET" refers to an enzyme that modifies cross-linking relationships between cellulose microfibrils and the xyloglucan matrix, and loosens the cell wall. Thus, a "xyloglucan endoglycosyltransferase" or "XET" of the invention is a subsequence or full length polynucleotide sequence of a gene which, when present in a transgenic plant, can be used to modify fiber quality (e.g., fiber length, fiber strength, or fiber fineness) and which is at least about 60%, 70%, 80%, 85%, 90%, 95%, 98% or more identical to SEQ ID NO:7. A XET polynucleotide typically comprises or consists of a coding region of at least about 30–40 nucleotides to about 1179 nucleotides in length. Usually, the nucleic acids are from about 100 to about 500 nucleotides, often from about 500 to about 1179 nucleotides in length.

"Pectin methyl esterase" or "PME" refers to an enzyme that is involved in esterification of the pectin matrix. Thus, a "pectin methyl esterase" or "PME" of the invention is a subsequence or full length polynucleotide sequence of a gene which, when present in a transgenic plant, can be used to modify fiber quality (e.g., fiber length, fiber strength, or fiber fineness) and which is at least about 60%, 70%, 80%, 85%, 90%, 95%, 98% or more identical to SEQ ID NO:9. A PME polynucleotide typically comprises or consists of a coding region of at least about 30–40 nucleotides to about 1702 nucleotides in length. Usually, the nucleic acids are from about 100 to about 500 nucleotides, often from about 500 to about 1702 nucleotides in length.

For any polypeptides described above, one of skill in the art will recognize that in light of the present disclosure, various modifications (e.g., substitutions, additions, and deletions) can be made to the polypeptide sequences without substantially affecting their function. These variations are within the scope of the present invention.

In the case of both expression of transgenes and inhibition of endogenous genes (e.g., by antisense, or sense suppression) one of skill will recognize that the inserted polynucleotide sequence need not be "identical," but may be only "substantially identical" to a sequence of the gene from which it was derived.

The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides, refers to two or more sequences or subsequences that have at least about 60%, or at least about 70%, preferably at least about 80%, most preferably at least about 90–98% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology*, F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403–410 and Altschuel et al. (1977) *Nucleic Acids Res.* 25: 3389–3402, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word bits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides are substantially identical is that the polypeptide encoded by the first nucleic acid is immunologically cross reactive with the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W). (see, e.g., Creighton, *Proteins* (1984)).

An indication that two nucleic acid sequences or polypeptides are substantially identical is that the polypeptide encoded by the first nucleic acid is immunologically cross reactive with the antibodies raised against the polypeptide encoded by the second nucleic acid. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, highly stringent conditions are selected to be about 5–10° C. lower than the thermal melting point ($T_m$) for the specific sequence at a defined ionic strength pH. Low stringency conditions are generally selected to be about 15–30° C. below the $T_m$. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, preferably 10 time background hybridization.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cased, the nucleic acids typically hybridize under moderately stringent hybridization conditions.

In the present invention, genomic DNA or cDNA comprising nucleic acids of the invention can be identified in standard Southern blots under stringent conditions using the nucleic acid sequences disclosed here. For the purposes of this disclosure, suitable stringent conditions for such hybridizations are those which include a hybridization in a buffer of 40% formamide, 1 M NaCl, 1% SDS at 37° C., and at least one wash in 0.2×SSC at a temperature of at least about 50° C., usually about 55° C. to about 60° C., for 20 minutes, or equivalent conditions. A positive hybridization is at least twice background. Those of ordinary skill will readily recognize that alternative hybridization and wash conditions can be utilized to provide conditions of similar stringency.

A further indication that two polynucleotides are substantially identical is if the reference sequence, amplified by a pair of oligonucleotide primers, can then be used as a probe under stringent hybridization conditions to isolate the test sequence from a cDNA or genomic library, or to identify the test sequence in, e.g., a northern or Southern blot.

"Fiber specific" promoter refers to promoters that preferentially promote gene expression in fiber cells over other cell types.

DETAILED DESCRIPTION

This invention provides plant FE genes that encode FE polypeptides, such as phosphoenol pyruvate carboxylase (PEPcase), expansin, endoglucanase, xyloglucan endoglycosyltransferase (XET), and pectin methyl esterase (PME). The invention further provides fiber-specific promoters. Still further, the invention provides molecular strategies for modulating fiber quality and yield in fiber producing plants by modulating expression of FE genes or mutant forms of FE genes.

Important fiber properties, such as fiber length, strength, and fineness, are determined by rate and duration of fiber expansion. Fiber expansion is, in turn, dependent primarily on cell turgor, the driving force of fiber expansion, and the extensibility of the cell wall. By manipulating genes that regulate these critical processes, fiber growth and fiber properties can be modified.

There are several genes encoding enzymes that are involved in maintaining turgor during fiber expansion. One such enzyme is phosphoenol pyruvate carboxylase (PEPcase). A PEPcase regulates synthesis of malate, which is a primary osmoregulatory solute involved in maintaining cell turgor during fiber expansion. By modulating the expression of PEPcase, the rate and/or duration of fiber expansion and fiber length can be regulated.

There are also several enzymes that regulate extensibility of fiber cell walls. These include: 1) expansins; 2) endoglucanases; 3) xyloglucan endoglycosyltransferases (XET); and 4) pectin methyl esterases (PME).

Expansins are thought to function in plant cell growth, cell wall disassembly, and cell separation. In particular, expansins influence cross-linking relationships in the cell wall and allow cell wall components to "slip" during fiber expansion, thereby allowing the fibers to increase in length. There are two classes of expansins that are currently recognized, alpha-expansins (EXP) and beta-expansins (EXPB). Alpha-expansins are a conserved group of proteins that function in cell wall enlargement and possibly other developmental processes including cell wall disassembly and cell separation. Beta-expansins are known to be secreted by grass pollen and have cell wall loosening effects on grass cells walls. It appears that one role of beta-expansins is to soften the stigma and stylar tissues to speed penetration of the pollen tubes through the maternal tissues to the ovule. Other beta-expansins are found in young grass seedlings and non-pollen tissue, thus, hinting at a variety of developmental functions of these proteins.

Generally, expansins are proteins with relatively conserved motifs. The mature protein may include two domains, a cysteine-rich region with limited sequence similarity to family-45 endoglucanases (EG45-like domain) and a tryptophan-rich carboxy terminus that may function as a putative polysaccharide-binding domain. Alpha-and beta-expansins share only about 20 to 25% amino acid sequence identity. The regions of identity are found throughout the protein backbone and include 6 of the 8 conserved cysteine residues in the cysteine-rich region, and the tryptophans near the carboxy terminus. Beta-expansins are glycosylated proteins while alpha-expansins are not glycosylated.

Studies in the small flowering plant, *Arabidopsis thaliana* (*A. thaliana*), have shown that the expansin gene family is extensive. *A. thaliana* contains 26 genes that encode alpha-expansin proteins, wherein these proteins are designated as EXP1 through EXP26. Most of the alpha-expansin genes have a conserved intron structure (i.e., two introns), wherein the intron lengths range from about 90 bp to about 500 bp. Some alpha-expansin genes (e.g., EXP17 through EXP26) are missing intron 2; EXP10 has an additional intron in the 5' untranslated region. *A. thaliana* also contains 5 genes that encode beta-expansin proteins which are designated EXPB1 through EXPB5. These genes typically contain three introns, of which two introns are conserved in alpha expansins, and a third intron that is not found in alpha-expansins and may be located before or after intron 2.

Alpha- and beta-expansin genes have been investigated in a number of species, including cucumber, rice, pea, tomato, strawberry, apricot, pine, tobacco, fern, and maize. Expansin proteins are also found in cotton such as in *Gossypium hirsutum* (*G. hirsutum*), in fact, there are two major isoforms such as GhEXP1 and GhEXP2. GhEXP1 (EpGhEX1), a full length cDNA, encodes a 258 amino acid alpha-expansin protein with a N-terminal signal peptide. The corresponding transcript is abundant in cotton fiber cells but absent in all other tissues tested. This gene is presumed to be developmentally regulated during fiber elongation in *G. hirsutum* (see Orford et al. (1998) *Biochem. Biophys. Acta.* 1398(3): 342–346).

The GhEXP2 cDNA (SEQ ID NO: 3) encodes a novel alpha expansin protein (SEQ ID NO: 4) from *G. hirsutum*. This novel GhEXP2 differs structurally from GhEXP1 and plays an important role in cell elongation. Overexpression of GhEXP2 shows significant gains in cotton yield and fiber quality (see Example 2, vide infra).

Other enzymes are involved in cell wall relaxation during fiber expansion. For example, an endoglucanase is a cellulase that cleaves glucan cellulose, thereby controlling the length of cellulose polymers. Changing the cellulose polymer length in primary cell walls of developing fibers can strongly influence fiber length. In another example, XETs are important in cell wall loosening, by changing cross-linking relationships between cellulose microfibrils and the xyloglucan matrix. In yet another example, PMEs are enzymes that are involved in esterification of the pectin matrix. The pectin matrix is highly esterified during rapid fiber expansion. When esterified pectin fraction is deesterified, it results in increased cell wall rigidity during the termination of fiber expansion. Not wishing to be bound by a theory, delaying the deesterification of this pectin fraction can increase the duration of fiber expansion, and hence, fiber length.

A single FE or any combinations of the FE nucleic acids encoding the above enzymes can be introduced into a plant to modulate the quality of fibers. Preferably, a fiber-specific promoter is used to express the FE nucleic acids only in fibers of plants. More preferably, an inducible fiber specific promoter is used to express these genes during appropriate developmental stages most likely to result in increased fiber growth.

Isolation of Nucleic Acids

Generally, the nomenclature and the laboratory procedures in recombinant DNA technology described below are those well known and commonly employed in the art. Standard techniques are used for cloning, DNA and RNA isolation, amplification and purification. Generally enzymatic reactions involving DNA ligase, DNA polymerase, restriction endonucleases and the like are performed according to the manufacturer's specifications. These techniques and various other techniques are generally performed according to Sambrook et al., *Molecular Cloning—A Laboratory Manual*, Cold Spring Harbor Laboratory, Cold Spring Harbor, N.Y., (1989) or Current Protocols in Molecular Biology Volumes 1–3, John Wiley & Sons, Inc. (1994–1998).

The isolation of nucleic acids may be accomplished by a number of techniques. For instance, oligonucleotide probes based on the sequences disclosed here can be used to identify the desired gene in a cDNA or genomic DNA library. To construct genomic libraries, large segments of genomic DNA are generated by random fragmentation, e.g. using restriction endonucleases, and are ligated with vector DNA to form concatemers that can be packaged into the appropriate vector. To prepare a cDNA library, mRNA is isolated from the desired organ, such as leaves, and a cDNA library which contains gene transcripts is prepared from the mRNA. Alternatively, cDNA may be prepared from mRNA extracted from other tissues in which genes of interest or their homologs are expressed.

The cDNA or genomic library can then be screened using a probe based upon the sequence of a cloned gene disclosed here. Probes may be used to hybridize with genomic DNA or cDNA sequences to isolate homologous genes in the same or different plant species. Alternatively, antibodies raised against a polypeptide of interest can be used to screen an mRNA expression library.

Alternatively, the nucleic acids of interest can be amplified from nucleic acid samples using amplification techniques. For instance, polymerase chain reaction (PCR) technology can be used to amplify the sequences of genes directly from genomic DNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. For a general overview of PCR, see *PCR Protocols: A Guide to Methods and Applications*. (Innis, M, Gelfand, D., Sninsky, J. and White, T., eds.), *Academic Press*, San Diego (1990). Appropriate primers and probes for identifying sequences from plant tissues are generated from comparisons of the sequences provided herein (e.g. SEQ ID NO: 1, SEQ ID NO:3, SEQ ID NO:5, SEQ ID NO:7, etc.).

Polynucleotides may also be synthesized by well-known techniques, as described in the technical literature. See, e.g., Carruthers et al, *Cold Spring Harbor Symp. Quant. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Increasing Levels of Gene Expression in Plant Fibers

The isolated nucleic acid sequences prepared as described herein can be used in a number of techniques. For example, the isolated nucleic acids can be introduced into plants to enhance endogenous gene expression. A particularly useful gene for this purpose is the FE genes shown in SEQ ID NO: 1, 3, 5, 7, and 9. In one embodiment, more than one gene can be introduced into plants. For example, expansins and endoglucanases can be expressed in plant fibers, thereby modifying crosslinking relationships and the cellulose polymer length in primary cell walls. Preferably, fiber tissues are targeted to increase expression FE genes. Fibers can be targeted at all times during the life of the plant e.g., using a constitutive promoter, or transiently, e.g., using a transiently active or an inducible promoter.

Isolated nucleic acids prepared as described herein can be used to introduce expression of particular FE nucleic acids to enhance endogenous gene expression. Enhanced expression will lead to increased fiber quality, such as fiber length, strength, and fineness; and increased fiber yield. Thus, plants comprising these constructs are particularly useful for producing fibers with improved properties for textile products. Where overexpression of a gene is desired, the desired gene from a different species may be used to decrease potential sense suppression effects. One of skill will recognize that the polypeptides encoded by the genes of the invention, like other proteins, have different domains which perform different functions. Thus, the gene sequences need not be full length, as long as the desired functional domain of the protein is expressed.

Modified protein chains can also be readily designed utilizing various recombinant DNA techniques well known to those skilled in the art and described in detail below. For example, the chains can vary from the naturally occurring sequence at the primary structure level by amino acid substitutions, additions, deletions, and the like. These modifications can be used in a number of combinations to produce the final modified protein chain.

In another embodiment, modified forms of genes disclosed here can be used that have increased activity in vivo. For example, endoglucanase mutants that elongate the cellulose polymer length can be created and used to produce transgenic plants. Additional hyperactive forms can be readily identified, e.g., by screening for modified forms of FE enzymes with an increased ability to modify fiber quality such as fiber length, strength, and fineness.

In another embodiment, endogenous gene expression can be targeted for modification. Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as X-rays or gamma rays can be used.

Alternatively, homologous recombination can be used to induce targeted gene modifications by specifically targeting the FE gene in vivo (see, generally, Grewal and Klar, *Genetics* 146: 1221–1238 (1997) and Xu et al., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al., *Nature* 389:802–803 (1997)).

In applying homologous recombination technology to the genes of the invention, mutations in selected portions of a FE gene sequence (including 5' upstream, 3' downstream, and intragenic regions) such as those disclosed herein are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91: 4303–4307 (1994); and Vaulont et al., *Transgenic Res.* 4: 247–255 (1995) are conveniently used to increase the efficiency of selecting for altered FE expression in transgenic plants. The mutated gene will interact with the target wild-type gene in such a way that homologous recombination and targeted replacement of the wild-type gene will occur in transgenic plant cells, resulting in increased FE activity.

Alternatively, oligonucleotides composed of a contiguous stretch of RNA and DNA residues in a duplex conformation with double hairpin caps on the ends can be used. The RNA/DNA sequence is designed to align with the sequence of the target gene and to contain the desired nucleotide change. Introduction of the chimeric oligonucleotide on an extrachromosomal T-DNA plasmid results in efficient and specific FE gene conversion directed by chimeric molecules in a small number of transformed plant cells. This method is described in Cole-Strauss et al., *Science* 273:1386–1389 (1996) and Yoon et al., *Proc. Natl. Acad. Sci. USA* 93: 2071–2076 (1996).

One method to increase activity of desired gene products is to use "activation mutagenesis" (see, e.g., Hiyashi et al. *Science* 258:1350–1353 (1992)). In this method an endogenous gene can be modified to be expressed constitutively, ectopically, or excessively by insertion of T-DNA sequences that contain strong/constitutive promoters upstream of the endogenous gene. Activation mutagenesis of the endogenous gene will give the same effect as overexpression of the transgenic nucleic acid in transgenic plants. Alternatively, an endogenous gene encoding an enhancer of gene product activity or expression of the gene can be modified to be expressed by insertion of T-DNA sequences in a similar manner and FE activity can be increased.

Another strategy to increase gene expression can involve the use of dominant hyperactive mutants of the gene by expressing modified transgenes. For example, expression of a modified FE with a defective domain that is important for interaction with a negative regulator of FE activity can be used to generate dominant hyperactive FE proteins. Alternatively, expression of truncated FE which have only a domain that interacts with a negative regulator can titrate the negative regulator and thereby increase endogenous FE activity. Use of dominant mutants to hyperactivate target genes is described, e.g., in Mizukami et al., *Plant Cell* 8:831–845 (1996).

Supression of FE Expression

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA*, 85:8805–8809 (1988), and Hiatt et al., U.S. Pat. No. 4,801,340.

The nucleic acid segment to be introduced generally will be substantially identical to at least a portion of the endogenous embryo-specific gene or genes to be repressed. The sequence, however, need not be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of embryo-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279–289 (1990), and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants which are overexpressers. A higher identity in a shorter than full length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

Preparation of Recombinant Vectors

To use isolated sequences in the above techniques, recombinant DNA vectors suitable for transformation of plant cells are prepared. Techniques for transforming a wide variety of higher plant species are well known and described in the technical and scientific literature. See, for example, Weising et al, *Ann. Rev. Genet.* 22:421–477 (1988). A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S and 19S transcription initiation regions; the full-length FMV transcript promoter (Gowda et al., *J Cell Biochem* 13D:301; the 1'- or 2'-promoter derived from T-DNA of *Agrobacterium tumefaciens*, and other transcription initiation regions from various plant genes known to those of skill. Such promoters and others are described, e.g. in U.S. Pat. No. 5,880,330. Such genes include for example, ACT11 from *Arabidopsis* (Huang et al, *Plant Mol. Biol.* 33:125–139 (1996)), Cat3 from *Arabidopsis* (GenBank No. U43147, Zhong et al., *Mol. Gen. Genet.* 251:196–203 (1996)), the gene encoding stearoyl-acyl carrier protein desaturase from *Brassica napus* (Genbank No. X74782, Solocombe et al. *Plant Physiol.* 104:1167–1176 (1994)), GPc1 from maize (GenBank No. X15596, Martinez et al. *J. Mol. Biol* 208:551–565 (1989)), and Gpc2 from maize (GenBank No. U45855, Manjunath et al., *Plant Mol. Biol.* 33:97–112 (1997)).

Alternatively, the plant promoter may direct expression of a nucleic acid in a specific tissue, organ or cell type (i.e., tissue-specific promoters) or may be otherwise under more precise environmental or developmental control (i.e., inducible promoters). Examples of environmental conditions that may effect transcription by inducible promoters include anaerobic conditions, elevated temperature, the presence of light, or sprayed with chemicals/hormones. Numerous inducible promoters are known in the art, any of which can be used in the present invention. Such promoters include the yeast metallothionine promoter, which is activated by copper ions (see, e.g., Mett et al. (1993) PNAS 90:4567), the dexamethasone-responsive promoter, In2–1 and In2–2, which are activated by substituted benzenesulfonamides, and GRE regulatory sequences, which are glucocorticoid-responsive (Schena et al., *Proc. Natl. Acad. Sci. U.S.A.* 88: 0421 (1991)).

Tissue-specific promoters can be inducible. Similarly, tissue-specific promoters may only promote transcription within a certain time frame of developmental stage within that tissue. Other tissue specific promoters may be active throughout the life cycle of a particular tissue. One of skill will recognize that a tissue-specific promoter may drive expression of operably linked sequences in tissues other than the target tissue. Thus, as used herein a tissue-specific promoter is one that drives expression preferentially in the target tissue or cell type, but may also lead to some expression in other tissues as well.

In preferred embodiments, promoters that drive fiber-specific expression of polynucleotides can be used. Such expression can be achieved under the control of the fiber-specific promoters described, for example, in U.S. Pat. No. 5,495,070. Typically, the nucleic acids of the invention are operably linked to a promoter active primarily during the stages of cotton fiber cell elongation, e.g., as described by Rinehart (1996) Plant Physiol. 112:1131–1141. See also, John (1997) Proc. Natl. Acad. Sci. USA 89:5769–5773; John, et al., U.S. Pat. Nos. 5,608,148 and 5,602,321, describing cotton fiber-specific promoters and methods for the construction of transgenic cotton plants.

Additional promoters which are linked to genes found to be expressed preferentially in cotton fiber cells can also be identified and isolated for incorporation into the expression cassettes and vectors of the invention. They care also used to express ABP nucleic acids in a cotton fiber specific (or fiber-preferential) manner. As the coding sequences for these tissue specific genes have been characterized, identification and isolation of these cotton fiber specific promoters can be accomplished using standard genetic engineering techniques. For example, Shimizu (1997) Plant Cell Physiol. 38:375–378, found that both endo-1,4-beta-glucanase and expansin mRNA levels were high during cotton fiber cell elongation, but decreased when cell elongation ceased. Xyloglucan also decreased. The endo-1,3-beta-glucanase mRNA level was very low in the elongating cells, but increased gradually at the onset of secondary wall synthesis, accompanying the massive deposition of cellulose. Also, as discussed above, Song (1997) supra, found a cotton fiber-specific acyl-carrier protein in *Gossypium hirsutum*. Ma (1997) Biochim. Biophys. Acta 1344:111–114, found a cotton fiber-specific cDNA encoding a lipid transfer protein. See also John, U.S. Pat. No. 5,597,718, describing means to identify cotton fiber-specific genes by differential cDNA library screenings.

Root-specific promoters may also be used in some embodiments of the present invention. Examples of root-specific promoters include the promoter from the alcohol dehydrogenase gene (DeLisle et al. Int. *Rev. Cytol.* 123, 39–60 (1990)).

Further examples include, e.g., ovule-specific, embryo-specific, endosperm-specific, integument-specific, seed coat-specific, or some combination thereof. A leaf-specific promoter has been identified in maize, Busk (1997) Plant J. 11:1285–1295. The ORF13 promoter from *Agrobacterium rhizogenes* exhibits high activity in roots (Hansen (1997) supra). A maize pollen-specific promoter has been identified, Guerrero (1990) Mol. Gen. Genet. 224:161–168). A tomato promoter active during fruit ripening, senescence and abscission of leaves and, to a lesser extent, of flowers can be used (Blume (1997) Plant J. 12:731–746); or a pistil-specific promoter from the potato SK2 gene, encoding a pistil-specific basic endochitinase (Ficker (1997) Plant Mol. Biol. 35:425–431). The Blec4 gene from pea is active in epidermal tissue of vegetative and floral shoot apices of transgenic alfalfa, making it a useful tool to target the expression of foreign genes to the epidermal layer of actively growing shoots or fibers. Another tissue-specific plant promoter is the ovule-specific BEL1 gene (Reiser (1995) Cell 83:735–742, GenBank No. U39944). See also Klee, U.S. Pat. No. 5,589,583, describing a plant promoter region is capable of conferring high levels of transcription in meristematic tissue and/or rapidly dividing cells.

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosulfuron or Basta.

Production of Transgenic Plants

DNA constructs of the invention may be introduced into the genome of the desired plant host by a variety of conventional techniques. For example, the DNA construct may be introduced directly into the genomic DNA of the plant cell using techniques such as electroporation and microinjection of plant cell protoplasts, or the DNA constructs can be introduced directly to plant tissue using ballistic methods, such as DNA particle bombardment.

Microinjection techniques are known in the art and well described in the scientific and patent literature. The introduction of DNA constructs using polyethylene glycol precipitation is described in Paszkowski et al. *Embo. J.* 3:2717–2722 (1984). Electroporation techniques are described in Fromm et al. *Proc. Natl. Acad. Sci. USA* 82:5824 (1985). Ballistic transformation techniques are described in Klein et al. *Nature* 327:70–73 (1987).

Alternatively, the DNA constructs may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. *Agrobacterium tumefaciens*-mediated transformation techniques, including disarming and use of binary vectors, are well described in the scientific literature. See, for example Horsch et al., *Science* 233:496–498 (1984), and Fraley et al. *Proc. Natl. Acad. Sci. USA* 80:4803 (1983) and *Gene Transfer to Plants*, Potrykus, ed. (Springer-Verlag, Berlin 1995).

Transformed plant cells which are derived by any of the above transformation techniques can be cultured to regenerate a whole plant which possesses the transformed genotype and thus the desired phenotype such as increased fiber length, strength or fineness. Such regeneration techniques rely on manipulation of certain phytohormones in a tissue culture growth medium, typically relying on a biocide and/or herbicide marker that has been introduced together with the desired nucleotide sequences. Plant regeneration from cultured protoplasts is described in Evans et al., *Protoplasts Isolation and Culture, Handbook of Plant Cell Culture*, pp. 124–176, MacMillilan Publishing Company, New York, 1983; and Binding, *Regeneration of Plants, Plant Protoplasts*, pp. 21–73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467–486 (1987).

The nucleic acids of the invention can be used to confer desired traits on essentially any fiber producing plants. These plants include cotton plants (*Gossypium arboreum, Gossypium herbaceum, Gossypium barbadense* and *Gossypium hirsutum*), silk cotton tree (*Kapok, Ceiba pentandra*), desert willow, creosote bush, winterfal, balsa, ramie, kenaf, hemp (*Cannabis sativa*), roselle, jute, sisal abaca and flax.

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

Using known procedures one of skill can screen for plants of the invention by detecting the increase or decrease of an mRNA or protein of interest in transgenic plants. Means for detecting and quantifying mRNAs or proteins are well known in the art.

Assessing Fiber Quality

Fibers produced from the transgenic plants transformed with FE nucleic acids are compared to control fibers (e.g., fibers from native plants or plants transformed with marker nucleic acids) to determine the extent of modulation of fiber properties. Modulation of fiber properties, such as fiber length, strength, or fineness, is achieved when the percent difference in these fiber properties of transgenic plants and control plants is at least about 10%, preferably at least about 20%, most preferably at least about 30%.

Several parameters can be measured to compare the properties or quality of fibers produced from transgenic plants transformed with FE nucleic acids and the quality of fibers produced from native plants. These include: 1) fiber length; 2) fiber strength; and 3) fineness of fibers.

A number of methods are known in the art to measure these parameters. See, e.g., U.S. Pat. No. 5,495,070, incorporated herein by reference. For example, instruments such as a fibrograph and HVI (high volume instrumentation) systems can be used to measure the length of fibers. The HVI systems can also be used to measure fiber strength. Fiber strength generally refers to the force required to break a bundle of fibers or a single fiber. In HVI testing, the breaking force is expressed in terms of "grams force per tex unit." This is the force required to break a bundle of fibers that is one tex unit in size. In addition, fineness of fibers can be measured, e.g., from a porous air flow test. In a porous air flow test, a weighed sample of fibers is compressed to a given volume and controlled air flow is passed through the sample. The resistance to the air flow is read as micronaire units. More specifically, the micronaire value is a measurement of cotton fiber quality that is a reflection of both fineness and maturity; low values indicate fine and/or immature fiber; high values indicate coarse and/or mature fibers. These values are determined according to standard techniques by measuring the resistance offered by a plug of cotton to airflow (supra) that is influenced by a combination of fineness and maturity. Fineness is the outside diameter of the fiber that is measured in mTex (Millitex or mg/km). Maturity is the degree of wall thickening of the fiber. Short fiber count (w) % refers to the percentage of short fiber weight; short fiber count (n) % refers to the percentage of short fiber yield. Immature fiber count refers to the number of immature fibers, i.e., fibers in which the thickening of the fiber wall is appreciably less than normal. An increase in fiber yield (fiber weight/seed) can be measured by using the Advanced Fiber Information System (AFIS). Using these and other methods known in the art, one of skill can readily determine the extent of modulation of fiber characteristics, quality and/or yield in transgenic plants.

EXAMPLES

The following examples are offered to illustrate, but not to limit the claimed invention.

Example 1

A full-length cDNA encoding a fiber-PEPC was isolated from a cotton fiber cDNA library. The characteristic features of the complete cDNA clone, designated PEPC1, are described below. PEPC1 gene expression in cotton was evaluated by RT-PCR using total RNA and clone specific primers (Table 1). PEPC1 was expressed in fibers, embryos, and roots, but not in the light-exposed tissues of leaves, bracts, petals, or stigma. The expression of PEPC1 was higher in fibers collected between 10 to 15 days post anthesis (DPA) when compared to the ovule, embryo and root tissues.

Developmental changes of PEPC1 expression in fiber (5 to 25 DPA) paralleled the rate of fiber elongation and peaked around the day of maximum cell expansion. Cotton PEPC1 showed a higher level of amino acid identity to the C3-type enzyme from plant species (86–89% identity and 5–7% similarity) compared to 76–86% identity to the C4-type enzyme. These observations suggest that the PEPC1 gene is tissue-specific and can be categorized as a C3-dark PEPC isoform.

The partial cotton PEPC cDNA clone of 577 bp encodes the C-terminal portion of the enzyme. Sequence comparison of PEPC1 and PEPC2 cDNAs showed 80% nucleotide identity, and the deduced amino acid sequences revealed 87% amino acid identity and 6.3% similarity. Overlapping sequence information confirmed that PEPC2 represents a second highly homologous PEPC gene expressed in developing cotton fibers (*Gossypium hirsufum* L.).

Cloning Techniques:

A λunizap II cDNA library, constructed from developing cotton fibers (10 days post-anthesis), was screened with a 577 by PCR product as a homologous hybridization probe. The PEPC2 cDNA probe was prepared by PCR-amplification with the primer-set, COT189 (5=-CCATG-GATCTTTGCCTGGAC-3=) (SEQ ID NO: 11) and COT185 (5=-GCATTCCAGCAGCAATACC-3=) (SEQ ID NO: 12), which were designed to conserved regions of PEPC in other plant organisms. The partial cDNA was cloned into pCRII. Both strands of the partial cDNA and the full-length cDNA in pBluescript SK (−) were sequenced by the dideoxy-chain termination method using vector-specific and synthetic oligonucleotide primers.

Comparison of the nucleotide and the deduced amino acid sequences to alfalfa (AC M83086), *Flaveria australasica* (AC Z25853), *Flaveria pringlef* (AC X64144), *Flaveria trinervia* (AC X64143), maize (AC X61489), potato (AC X67053), rape seed (AC D13987), sorghum (AC X65137), sorghum (AC X59925), soybean (AC D10717), and tobacco (AC X59016) homologs.

The PEPC1 cDNA is 3405 bp in length, containing 288 bp 5=-UTR, 2898 bp coding region, and 219 by 3=-UTR. Translation start and stop codons are positioned at nucleotides 289 and 3184, respectively. 44.7% (G+C) content in protein coding region.

The 2898-by open reading frame of PEPC1 encodes a polypeptide of 965 amino acids with a predicted Mr of 110,183, an isoelectric point of 5.95, and an aliphatic index of 88.54. The total numbers of negatively charged (ASP+GLU) and positively charged (ARG+LYS) residues are 143 and 127, respectively. There is a conserved phosphorylation site at residue 11 (Ser). His-172 and Lys-600, which are essential for enzyme activity, are located in conserved motifs (Chollet et al., 1996). The deduced amino acid sequence exhibits a 79–89% identity and a 5.3–6.9% similarity to the PEPC of other plants.

Protein Homology:

Alignment of PEPC amino acids (data not shown) reveals some highly conserved regions between these enzymes, which are distributed along the protein. A glycine-rich motif, FHGRGGXXGRGG (SEQ ID NO: 13), found in all PEPC enzymes, is proposed to be involved in the binding of PEP (Iterada et al., 1992). Another highly conserved sequence, GYSDSXKDXG (SEQ ID NO: 14), contains the lysine residue implicated in the activity of PEPC (Jiao et al., 1990). The VXTAHPT (SEQ ID NO: 15) motif (amino acid 168–174) contains a histidine residue, which has been suggested to be essential for activity (Chollet et al., 1996; Andreo et al., 1987). Furthermore, a sequence closely related to the phosphorylation site, E/DK/R-X-X-SIDAQLR (SEQ ID NOS: 16–18) (Jiao et al., 1990), which is conserved in C3 and C4 plants, is also found in the N-terminal region of the cotton PEPC. It is suggested that non photosynthetic PEPCs from C3 and C4 plants undergo regulatory phosphorylation similar to their C4 and CAM photosynthetic counterparts (Lepiniec et al., 1994).

Expression Characteristics:

The expression of PEPC in different tissues (fiber, embryo, root, leaf, bract, petal and stigma) was tested by quantitative RT-PCR using 500 ng total RNA and a set of clone-specific primers, COT 285 (5=-CTTTCTGCGGAG-TACGAAG-3=) (SEQ ID NO: 19) and COT 288 (5=-CCTGCTCTCATCTCATCTTG-3=) (SEQ ID NO: 20). PEPC1 was expressed in fibers, embryos, and roots but not in the light-exposed tissues of leaves, bracts, petals, or stigma. The developmental expression of PEPC1 in fiber peaked around the day of maximum fiber elongation.

Example 2

A fiber cDNA (GhEXP2) (SEQ ID NO: 3) encoding an expansin protein (SEQ ID NO: 4) was isolated from a cotton fiber cDNA library and sequenced. Expansin plays an important role in cell elongation and was targeted for ectopic expression as a potential means for improving traits. The results showed significant gains in cotton yield and all fiber quality properties and provided evidence that cotton plants can be successfully manipulated in order to alter specific traits in a desired direction.

Cotton Fiber Development:

Scanning electron micrographs have shown that fibers begin to grow and elongate coincident with opening of the flower on the day of anthesis. Fiber growth in the first few days post-anthesis (dpa) has been shown to occur via a diffuse-growing mechanism (Tiwari and Wilkins (1995) *Can. J. Bot.* 73:746–757). By 5 dpa, fibers begin to undergo a period of sustained and rapid cell elongation for 15–20 days, reaching maximum rates of elongation >2 mm/day. A proprietary Cotton Fiber dbEST (i.e., a data base with cotton fiber expressed sequence tags), containing about 43,000 sequences, was developed. By using this database it was determined that the genetic complexity in rapidly elongating cotton fibers is high, i.e., requiring about 13,000 unique gene sequences. The fiber genes expressed during fiber elongation represent more than 30% of the cotton genome. It was also determined that expansin is among one of the most abundant gene transcripts expressed in elongating cotton fibers.

Role of Expansin:

The rigid primary cell wall of plant cells consists of cellulose microfibrils embedded in a matrix of non-cellulose polysaccharides. Cell expansion is driven by turgor pressure and the coordinate regulation of cell wall relaxation. Expansins are a family of cell wall proteins that act to relax the bonds between the cellulose microfibrils and cell wall polymers to allow sufficient slippage and deposition of newly synthesized cell wall materials. The differentially regulated members of the expansin gene family are associated with auxin-mediated cell expansion in various cell-and tissue-types in dicots. Hence, expansin provided an attractive target for altering cell size and shape.

Vector Construction:

A 35S::GhEXP2 vector construct was made by employing standard molecular biology recombinant DNA techniques (Sambrook et al. (2000) Molecular Cloning: A Laboratory Manual (Third Edition); Cold Spring Harbor Laboratory Press). A binary vector which includes an enhanced 35S promoter was used for the vector construct and made according to standard laboratory techniques. The cDNA sequence for expansin, GhEXP2, was isolated from a cotton fiber cDNA library (a λunizap II cDNA library was constructed from developing G. hirsutum cotton fiber at 10 days post-anthesis). GhEXP2 was cloned into the binary vector and then purified according to standard laboratory techniques (supra).

The GhEXP2 cDNA is 1153 bp in length and encodes an expansin polypeptide of 258 amino acids. A sequence alignment of the expansin polypeptide from GhEXP2 with alpha-expansin precursors (see NCBI, GI:21314545, GI:2134543) and GhEXP1 (see Orford et al., supra, GI:2811278) exhibits about 84–86% amino acid identity.

Ectopic Overexpression of Expansin in Transgenic Cotton:

The 35S::GhEXP2 vector construct was introduced into cotton by standard *Agrobacterium*-mediated co-cultivation of seedling hypocotyls (Agro strain LBA4404). Transgenic cotton plants were selected on kanamycin. Regeneration of T0 kanamycin-resistant plants was accomplished via somatic embryogenesis in about 10–12 month. Selection of fertile, kanamycin-resistant plants was made following confirmation of the presence of the intact transgene at the molecular level.

Fiber Analysis:

Cotton seed (i.e., seed and fiber) was harvested from mature bolls grown in the greenhouse. Fiber and seed were weighed. Then fiber was removed from the seed by hand. Fiber and seed were again weighed separately which provided data for some of the yield components. The fiber was shipped to a fiber analysis lab (Cotton Inc.) where fiber properties were measured using standard procedures. The measurements were performed by using the Advanced Fiber Information System (AFIS) as employed in the art.

Results:

The results showed significant gains in yield and fiber quality of T1 transgenic cotton plants that overexpress expansin. Wild type cotton plants (control) were compared to T0 kanamycin-resistant plants and T1 transgenic plants. The T1 transgenic plants showed a 4 fold increase in yield (fiber weight/seed); an increase in fiber length by about 0.2 inch (gains measured in 0.01 inch); a 50% decrease in immature fibers (i.e., increased number of mature fibers); and a 50% decrease in short fibers (i.e., increased fiber uniformity).

There was a dramatic increase in the number of fiber initials in overexpressing expansin transgenic plants relative to wild type control (untransformed) plants as determined through scanning electron micropgraphs. The length of fiber initials in transgenic plants at 0 dpa (anthesis) was also increased by at least a factor of 2. Thus, increased yield in transgenic plants is due in part to an increase in fiber number/seed.

As shown above, ectopic overexpression of a single gene encoding the cell wall protein expansin successfully and significantly improved complex agronomic traits such as yield and fiber quality.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated nucleic acid molecule comprising a recombinant expression cassette comprising a plant promoter operably linked to a heterologous expansin polynucleotide sequence which encodes a polypeptide which is at least about 95% identical to SEQ ID NO: 4, wherein the isolated nucleic acid molecule increases fiber quality and/or yield in a cotton plant.

2. The isolated nucleic acid molecule of claim 1, wherein the expansin polynucleotide comprises SEQ ID NO: 3.

3. The isolated nucleic acid molecule of claim 1, wherein the nucleic acid encodes an expansin polypeptide having SEQ ID NO: 4.

4. The isolated nucleic acid molecule of claim 1, wherein the plant promoter is a tissue-specific promoter.

5. The isolated nucleic acid molecule of claim 4, wherein the promoter is a fiber-specific promoter.

6. The isolated nucleic acid molecule of claim 1, wherein the promoter is an inducible promoter.

7. A transgenic cotton plant comprising an expression cassette containing a plant promoter operably linked to a heterologous expansin polynucleotide sequence, which encodes a polypeptide which is at least about 95% identical to SEQ ID NO: 4.

8. The transgenic plant of claim 7, wherein the expansin polynucleotide encodes an expansin polypeptide.

9. The transgenic plant of claim 7, wherein the expansin polypeptide has the amino acid sequence of SEQ ID NO: 4.

10. The transgenic plant of claim 7, wherein the plant promoter is a tissue specific promoter.

11. The transgenic plant of claim 10, wherein the promoter is a fiber-specific promoter.

12. The transgenic plant of claim 11, wherein the promoter is a cotton fiber specific promoter.

13. The transgenic plant of claim 7, wherein the expensin polynucleotide has the nucleic acid sequence of SEQ ID NO: 3.

14. A method of increasing fiber quality and/or yield in a cotton plant, the method comprising introducing into the plant an expression cassette containing a plant promoter operably linked to a heterologous expansin polynucleotide sequence, which encodes a polypeptide which is at least about 95% identical to SEQ ID NO: 4.

15. The method of claim 14, wherein the heterologous expansin polynucleotide has the nucleic acid sequence of SEQ ID NO:3.

16. The method of claim 14, wherein the plant promoter is a tissue specific promoter.

17. The method of claim 16, wherein the promoter is a fiber specific promoter.

18. The method of claim 17, wherein the promoter is a cotton fiber specific promoter.

19. The method of claim 14, wherein the expression cassette is introduced into the plant through a sexual cross.

20. The method of claim 14, wherein the heterologous expansin polynucleotide encodes an expansin polypeptide.

* * * * *

SEQUENCE LISTING

```
<160> NUMBER OF SEQ ID NOS: 25

<210> SEQ ID NO 1
<211> LENGTH: 3405
<212> TYPE: DNA
<213> ORGANISM: Artificial Sequence
<220> FEATURE:
<223> OTHER INFORMATION: PEPCase: Cotton + 10 dpa Fiber cDNA

<400> SEQUENCE: 1
tttcactttc tggtgttcag tcataagtta cccattattt tatctgtttt tctagcgatt      60
tcttggtgtg gggcatcacg gaattcactt ccaaagagat aggatttgat tcatcttttg     120
ttttccgggt ttgggtttgg gttcggcgga ttcttcgcca caaattattt ttatcctttt     180
acaccgcaaa ataataaatt tcatccgtaa ttgttccttt ctttttcctg cctttcattg     240
gttcataatt taaagttttg gctttggtag tcaagtaaaa agacagagat ggcaggtaga     300
aaagtagaga agatggcttc aatagatgca caactaaggc tattagcacc tgggaaagtc     360
tctgaggatg ataagttggt tgaatatgat gctgtgctac tggatcgttt tcttgatatt     420
cttcaggatt tgcatggaga ggatatcaga gaaacggttc aagaatgcta cgagctttct     480
```

-continued

| | |
|---|---|
| gcggagtacg aaggaaagca tgatcctaaa atattggagg agcttggcaa ggtacttaca | 540 |
| agcttggatc ctggggactc aattgttgtt accaaatcat tttcccacat gcttaacttg | 600 |
| ggaaacttgg ccgaggaggt tcaaattgca tatagacgaa ggattaagtt gaagaaagga | 660 |
| gattttgctg atgagagttc agcaacaact gaatcagata ttgaagagac gttcaagcga | 720 |
| cttgtgggc agttgaacaa gtcccctgaa gaagttttg atgctttgaa gaatcagact | 780 |
| gtagatttag tcttaactgc acatcctaca cagtctgttc gaagatcttt acttcaaaaa | 840 |
| cacggaagga tacgtaattg tttgacacaa ttgtatgcta agacattac acctgatgat | 900 |
| aagcaggaac ttgatgaggc actacaaagg gagattcaag ctgctttcg cacagatgag | 960 |
| atccgaagga atcctcccac cccacaagat gagatgagag caggaatgag ctacttccac | 1020 |
| gagacaatct ggaaaggtgt accaaaattc ttgcgtcgtg ttgacacagc tttgaagaac | 1080 |
| atagggataa atgaacgtgt tccatacaat gcccctctta ttcaattctc ttcatggatg | 1140 |
| ggagggatc gtgatggaaa ccccagggta actcctgaag ttacaagaga tgtctgctta | 1200 |
| ttagctagaa tgatggctgc taacttgtac ttctcccaaa tagaggatct tatgtttgag | 1260 |
| ttatcaatgt ggcgttgcag cgatgaactt cgtattcgtg cagatgaact ccataggtcc | 1320 |
| tccaaaaagg atgcaaagca ttacatagaa ttttggaaac agattcctcc aaatgagcca | 1380 |
| tatcgcatta ttcttggtga tgtgagggac aagctgtata atacacgtga acgtgctcgt | 1440 |
| agcctgttgg ccaatggatt ttctgacatt cctgaagaag cagcatttac caatgtggag | 1500 |
| cagtttctgg agcctcttga actctgctat agatcactct gtgcttgtgg tgatcggcca | 1560 |
| atagctgatg gaagccttct tgatttctta cggcaagttt ctacctttgg gctttcactt | 1620 |
| gtgaggcttg atatccgaca ggaatctgat agacatactg atgtccttga tgctatcaca | 1680 |
| aagcacctgg atattggatc ttatcgagaa tggcctgagg aacgccgaca ggaatggctc | 1740 |
| ttatctgaac tcagaggcaa gcgccctcta ttcggccctg atcttcccaa aacagaagaa | 1800 |
| gtcgctgatg tattggacac atttcatgtc atttctgaac tgccttcaga cagctttggt | 1860 |
| gcctatataa tctcaatggc tacagcccca tctgatgtgc ttgctgttga gcttttacaa | 1920 |
| cgtgaatgcc atgtaaagca accattacgg gtagttccat gtttgaaaa actcgctgat | 1980 |
| cttgaagctg ctcctgctgc tgtggctcgt ctcttctcta tagattggta cagagaccgg | 2040 |
| atcaatggga aacaggaagt gatgataggt tattcagatt caggaaagga tgctggccgt | 2100 |
| ctttctgcag catggcagct atacaaggct caggaggaac ttgtaaaggt ggcaaagcag | 2160 |
| tatggtgtta agcttacaat gttccatggc cgaggaggga cagttggaag aggaggggga | 2220 |
| cccacgcatc ttgctatatt gtctcaacca cccgatacaa ttcatggatc acttcgtgta | 2280 |
| acagttcaag gtgaagttat tgaacaatca tttggagagg agcacttgtg cttcaggacg | 2340 |
| cttcaacgtt ttactgctgc tacacttgag catggaatgc atccccctgt ctcaccaaat | 2400 |
| ccagaatggc gtgcactcat ggatgaaatg gcagtagttg caacaaagga ataccgttct | 2460 |
| gtagtcttcc aggaacctcg ctttgttgaa tacttccgcc tagcaacacc agaattggag | 2520 |
| tatggtcgga tgaatattgg aagccgtcca tcaaaaagga aaccagtgg aggcattgaa | 2580 |
| tcactccgtg caatcccatg gatctttgca tggactcaaa caagatttca tttacctgtg | 2640 |
| tggcttggct ttggggctgc atttaagcac gtcattcaga aggatataaa gaatctccac | 2700 |
| atgctccagg agatgcacaa ccaatggcct ttctttaggg tcacaatgga cttaattgaa | 2760 |
| atggtatttg ccaagggaga ccctggaatc gctgccttat atgacaagct gctagtgtca | 2820 |
| aaggaactct ggcccttggg agagaacttg agagctaact atgaagacac taaacgactt | 2880 |

-continued

```
gttctccagg ttgctggaca cagagatctt cttgaaggtg acccttacct gaagcagagg    2940
ctccgacttc gtgatgctta catcacaacc cttaatgtgt gccaagcgta cactttgaaa    3000
aggatccgtg accctgatta tcatgtcaag gtcaggcctc acttatccag ggaatacatg    3060
gaatcaagca aggcggcagc tgagcttgtg aaacttaacc ctacaagcga gtatgctcct    3120
ggtctggaag acacccttat tttgaccatg aagggtattg ctgctggaat gcaaaacact    3180
ggttaaaact tgcggattgt tgtttccttg tgttgttatg ctccttagtt tattttaat    3240 ggatgttgct ttgcgtcaag taaaccttt atattactat tattatcggt tgggttaatt     3300
tcatatttgg ctcatatatt actaagtgtt gtcagtctgg tatctctata ataatacata    3360
ttaacatgat ttcccattca aaaaaaaaa aaaaaaaaa aaaaa                      3405
```

<210> SEQ ID NO 2
<211> LENGTH: 965
<212> TYPE: PRT
<213> ORGANISM: Artificial Sequence
<220> FEATURE:
<223> OTHER INFORMATION: PEPCase protein sequence

<400> SEQUENCE: 2

```
Met Ala Gly Arg Lys Val Glu Lys Met Ala Ser Ile Asp Ala Gln Leu
1               5                   10                  15

Arg Leu Leu Ala Pro Gly Lys Val Ser Glu Asp Asp Lys Leu Val Glu
            20                  25                  30

Tyr Asp Ala Val Leu Leu Asp Arg Phe Leu Asp Ile Leu Gln Asp Leu
        35                  40                  45

His Gly Glu Asp Ile Arg Glu Thr Val Gln Glu Cys Tyr Glu Leu Ser
    50                  55                  60

Ala Glu Tyr Glu Gly Lys His Asp Pro Lys Ile Leu Glu Glu Leu Gly
65                  70                  75                  80

Lys Val Leu Thr Ser Leu Asp Pro Gly Asp Ser Ile Val Val Thr Lys
                85                  90                  95

Ser Phe Ser His Met Leu Asn Leu Gly Asn Leu Ala Glu Glu Val Gln
            100                 105                 110

Ile Ala Tyr Arg Arg Arg Ile Lys Leu Lys Lys Gly Asp Phe Ala Asp
        115                 120                 125

Glu Ser Ser Ala Thr Thr Glu Ser Asp Ile Glu Glu Thr Phe Lys Arg
    130                 135                 140

Leu Val Gly Gln Leu Asn Lys Ser Pro Glu Glu Val Phe Asp Ala Leu
145                 150                 155                 160

Lys Asn Gln Thr Val Asp Leu Val Leu Thr Ala His Pro Thr Gln Ser
                165                 170                 175

Val Arg Arg Ser Leu Leu Gln Lys His Gly Arg Ile Arg Asn Cys Leu
            180                 185                 190

Thr Gln Leu Tyr Ala Lys Asp Ile Thr Pro Asp Asp Lys Gln Glu Leu
        195                 200                 205

Asp Glu Ala Leu Gln Arg Glu Ile Gln Ala Ala Phe Arg Thr Asp Glu
    210                 215                 220

Ile Arg Arg Asn Pro Pro Thr Pro Gln Asp Glu Met Arg Ala Gly Met
225                 230                 235                 240

Ser Tyr Phe His Glu Thr Ile Trp Lys Gly Val Pro Lys Phe Leu Arg
                245                 250                 255

Arg Val Asp Thr Ala Leu Lys Asn Ile Gly Ile Asn Glu Arg Val Pro
            260                 265                 270
```

-continued

Tyr Asn Ala Pro Leu Ile Gln Phe Ser Ser Trp Met Gly Gly Asp Arg
            275                 280                 285

Asp Gly Asn Pro Arg Val Thr Pro Glu Val Thr Arg Asp Val Cys Leu
        290                 295                 300

Leu Ala Arg Met Met Ala Ala Asn Leu Tyr Phe Ser Gln Ile Glu Asp
305                 310                 315                 320

Leu Met Phe Glu Leu Ser Met Trp Arg Cys Ser Asp Glu Leu Arg Ile
                325                 330                 335

Arg Ala Asp Glu Leu His Arg Ser Ser Lys Lys Asp Ala Lys His Tyr
            340                 345                 350

Ile Glu Phe Trp Lys Gln Ile Pro Pro Asn Glu Pro Tyr Arg Ile Ile
        355                 360                 365

Leu Gly Asp Val Arg Asp Lys Leu Tyr Asn Thr Arg Glu Arg Ala Arg
            370                 375                 380

Ser Leu Leu Ala Asn Gly Phe Ser Asp Ile Pro Glu Glu Ala Ala Phe
385                 390                 395                 400

Thr Asn Val Glu Gln Phe Leu Glu Pro Leu Glu Leu Cys Tyr Arg Ser
                405                 410                 415

Leu Cys Ala Cys Gly Asp Arg Pro Ile Ala Asp Gly Ser Leu Leu Asp
            420                 425                 430

Phe Leu Arg Gln Val Ser Thr Phe Gly Leu Ser Leu Val Arg Leu Asp
        435                 440                 445

Ile Arg Gln Glu Ser Asp Arg His Thr Asp Val Leu Asp Ala Ile Thr
    450                 455                 460

Lys His Leu Asp Ile Gly Ser Tyr Arg Glu Trp Pro Glu Glu Arg Arg
465                 470                 475                 480

Gln Glu Trp Leu Leu Ser Glu Leu Arg Gly Lys Arg Pro Leu Phe Gly
                485                 490                 495

Pro Asp Leu Pro Lys Thr Glu Glu Val Ala Asp Val Leu Asp Thr Phe
            500                 505                 510

His Val Ile Ser Glu Leu Pro Ser Asp Ser Phe Gly Ala Tyr Ile Ile
        515                 520                 525

Ser Met Ala Thr Ala Pro Ser Asp Val Leu Ala Val Glu Leu Leu Gln
530                 535                 540

Arg Glu Cys His Val Lys Gln Pro Leu Arg Val Val Pro Leu Phe Glu
545                 550                 555                 560

Lys Leu Ala Asp Leu Glu Ala Ala Pro Ala Ala Val Ala Arg Leu Phe
                565                 570                 575

Ser Ile Asp Trp Tyr Arg Asp Arg Ile Asn Gly Lys Gln Glu Val Met
            580                 585                 590

Ile Gly Tyr Ser Asp Ser Gly Lys Asp Ala Gly Arg Leu Ser Ala Ala
        595                 600                 605

Trp Gln Leu Tyr Lys Ala Gln Glu Glu Leu Val Lys Val Ala Lys Gln
610                 615                 620

Tyr Gly Val Lys Leu Thr Met Phe His Gly Arg Gly Gly Thr Val Gly
625                 630                 635                 640

Arg Gly Gly Gly Pro Thr His Leu Ala Ile Leu Ser Gln Pro Pro Asp
                645                 650                 655

Thr Ile His Gly Ser Leu Arg Val Thr Val Gln Gly Glu Val Ile Glu
            660                 665                 670

Gln Ser Phe Gly Glu Glu His Leu Cys Phe Arg Thr Leu Gln Arg Phe
        675                 680                 685

-continued

```
Thr Ala Ala Thr Leu Glu His Gly Met His Pro Pro Val Ser Pro Asn
        690                 695                 700
Pro Glu Trp Arg Ala Leu Met Asp Glu Met Ala Val Val Ala Thr Lys
705                 710                 715                 720
Glu Tyr Arg Ser Val Val Phe Gln Glu Pro Arg Phe Val Glu Tyr Phe
                725                 730                 735
Arg Leu Ala Thr Pro Glu Leu Gly Tyr Gly Arg Met Asn Ile Gly Ser
            740                 745                 750
Arg Pro Ser Lys Arg Lys Pro Ser Gly Gly Ile Glu Ser Leu Arg Ala
        755                 760                 765
Ile Pro Trp Ile Phe Ala Trp Thr Gln Thr Arg Phe His Leu Pro Val
770                 775                 780
Trp Leu Gly Phe Gly Ala Ala Phe Lys His Val Ile Gln Lys Asp Ile
785                 790                 795                 800
Lys Asn Leu His Met Leu Gln Glu Met His Asn Gln Trp Pro Phe Phe
                805                 810                 815
Arg Val Thr Met Asp Leu Ile Glu Met Val Phe Ala Lys Gly Asp Pro
            820                 825                 830
Gly Ile Ala Ala Leu Tyr Asp Lys Leu Leu Val Ser Lys Glu Leu Trp
        835                 840                 845
Pro Phe Gly Glu Asn Leu Arg Ala Asn Tyr Glu Asp Thr Lys Arg Leu
850                 855                 860
Val Leu Gln Val Ala Gly His Arg Asp Leu Leu Glu Gly Asp Pro Tyr
865                 870                 875                 880
Leu Lys Gln Arg Leu Arg Leu Arg Asp Ala Tyr Ile Thr Thr Leu Asn
                885                 890                 895
Val Cys Gln Ala Tyr Thr Leu Lys Arg Ile Arg Asp Pro Asp Tyr His
            900                 905                 910
Val Lys Val Arg Pro His Leu Ser Arg Glu Tyr Met Glu Ser Ser Lys
        915                 920                 925
Ala Ala Ala Glu Leu Val Lys Leu Asn Pro Thr Ser Glu Tyr Ala Pro
930                 935                 940
Gly Leu Glu Asp Thr Leu Ile Leu Thr Met Lys Gly Ile Ala Ala Gly
945                 950                 955                 960
Met Gln Asn Thr Gly
            965

<210> SEQ ID NO 3
<211> LENGTH: 1153
<212> TYPE: DNA
<213> ORGANISM: Gossypium hirsutum
<220> FEATURE:
<221> NAME/KEY: misc_feature
<223> OTHER INFORMATION: Expansin cDNA

<400> SEQUENCE: 3
ggcacgaggg tcagccaatt gtttgagcta gctagctctt actcaaatgg caaccaaaac    60
gatgatgttg caaatatttt cacttttctt cttttttgttc agtatctgca actccatttt   120
ccttggtgct aatggagatg acaatggtgg ttggcaaact gcccatgcca ccttctacgg   180
tggtgctgat gctaccggca caatgggggg agcttgtggt tatggaaacc tgtacagtca   240
agggtatgga acgagcacag cagctttgag cactgcactt tcaacaatg gcttgagctg    300 cggtgccttc tacagctcc ggtgcaacaa tgatcctcaa tggtgcatta gtcgaaccat    360
aaccgtgaca gccaccaact tttgtccccc taactatgct ttatctagtg acaatggcgg    420
```

```
gtggtgcaat ccccacgag aacactttga tttggccgaa ccggcattct tgcagatcgc    480
ggaatatcga gctgggatcg tccctgttat gttcagaagg gtgtcatgtg tgaagaaagg    540
aggcatcagg tacaccatga atggacattc gtacttcaac atggtgttga taaccaacgt    600
gggaggggca ggggatataa cgtcagtgtc catcaagggt tccaaaacag gatggctacc    660
tatgtccaga aattggggcc aaaactggca gagcaatgct taccttaacg gccaaagcct    720
ctctttcaaa gtgactgcca gcgatagcag gactatcaca aactcaaatg tagtgcccgc    780
tggttggcaa ttcggacaaa cttttgaagg aggccagttt taagacaata ttatagtgtc    840
cgtctaatat taaaactgga attgacatat tacttatata aggcacatga gcgttttatg    900
ccgaggtagc aaagtggcgc ccgctggctt tatgtgtgaa ataggcgagc aagtgccatt    960
agcctataat atacacattt cctatagtga accaaactat taagtttgaa ctctagaagt   1020
gatatccata atgtctgaaa tttgattgtt gatgattgac catgatattt atggttttca   1080
ttattgaaat acttttttat tataatttat aaataaatga atcatttctt tttacaaaaa   1140
aaaaaaaaaa aaa                                                      1153
```

<210> SEQ ID NO 4
<211> LENGTH: 258
<212> TYPE: PRT
<213> ORGANISM: Gossypium hirsutum
<220> FEATURE:
<221> NAME/KEY: misc_feature
<223> OTHER INFORMATION: Expansin protein

<400> SEQUENCE: 4

```
Met Ala Thr Lys Thr Met Met Leu Gln Ile Phe Ser Leu Phe Phe Phe
 1               5                  10                  15

Leu Phe Ser Ile Cys Asn Ser Ile Phe Leu Gly Ala Asn Gly Asp Asp
            20                  25                  30

Asn Gly Gly Trp Gln Thr Ala His Ala Thr Phe Tyr Gly Gly Ala Asp
        35                  40                  45

Ala Thr Gly Thr Met Gly Gly Ala Cys Gly Tyr Gly Asn Leu Tyr Ser
    50                  55                  60

Gln Gly Tyr Gly Thr Ser Thr Ala Ala Leu Ser Thr Ala Leu Phe Asn
65                  70                  75                  80

Asn Gly Leu Ser Cys Gly Ala Phe Tyr Glu Leu Arg Cys Asn Asn Asp
                85                  90                  95

Pro Gln Trp Cys Ile Ser Arg Thr Ile Thr Val Thr Ala Thr Asn Phe
           100                 105                 110

Cys Pro Pro Asn Tyr Ala Leu Ser Ser Asp Asn Gly Gly Trp Cys Asn
       115                 120                 125

Pro Pro Arg Glu His Phe Asp Leu Ala Glu Pro Ala Phe Leu Gln Ile
   130                 135                 140

Ala Glu Tyr Arg Ala Gly Ile Val Pro Val Met Phe Arg Arg Val Ser
145                 150                 155                 160

Cys Val Lys Lys Gly Gly Ile Arg Tyr Thr Met Asn Gly His Ser Tyr
                165                 170                 175

Phe Asn Met Val Leu Ile Thr Asn Val Gly Gly Ala Gly Asp Ile Thr
           180                 185                 190

Ser Val Ser Ile Lys Gly Ser Lys Thr Gly Trp Leu Pro Met Ser Arg
       195                 200                 205

Asn Trp Gly Gln Asn Trp Gln Ser Asn Ala Tyr Leu Asn Gly Gln Ser
   210                 215                 220
```

```
Leu Ser Phe Lys Val Thr Ala Ser Asp Ser Arg Thr Ile Thr Asn Tyr
225                 230                 235                 240

Asn Val Val Pro Ala Gly Trp Gln Phe Gly Gln Thr Phe Glu Gly Gly
                245                 250                 255

Gln Phe
```

<210> SEQ ID NO 5
<211> LENGTH: 2386
<212> TYPE: DNA
<213> ORGANISM: Gossypium hirsutum
<220> FEATURE:
<221> NAME/KEY: misc_feature
<223> OTHER INFORMATION: 10 dpa fiber cDNA encoding Korrigan homolog
      from Arabidopsis

<400> SEQUENCE: 5

```
ggcacgagcc actttggaaa accaatgaag aaagcaccac tgcctactta tacacatttt      60
atttatcaaa ctcaacttcc tcttcgtctt ggtagatcag atctgtcggt gctcctgcat     120
tttccgccca ctactcttcc aaatcctcat catgtacggc agaaatccgt ggggaggtcc     180
cctggagata aacgccactg attctgccac tgacgacgac aggagcagga atctgcagga     240
cctggatagg gctgcactct ctcgcccctt ggacgagact cagcaaagct ggctgcttgg     300
ccccggggag caaagaaaga agaagaagta cgttgatctc ggatgtatca ttgtgagccg     360
caagatcttt gtatggaccg tggggaccct gctagtctcc gccctcctgg ccggactcat     420
caccctcatc gtcaagactg tcccacgtca tcaccaccgc cactctccgc cgataactac     480
cactctggct cttcacaagg cgctcatgtt ctttaatgct cagcgttctg gaaagctgcc     540
caagcataat aatgtgtcgt ggagagggaa ctcgggcctc aagatggcaa atccgatcc      600
ctccgttttg atgaaagatc tggtcggcgg atattacgat gctggagatg ctatcaagtt     660
taactttcct gcatctttttt caatgactat gttgagctgg agtgtcatcg aatacagtgc     720
taaatacgag gctgccggcg agctcaatca tgttaaagag atcatcaaat ggggtactga     780
ttatcttctg aagaccttca acaatactgc tgataccatt gacaggattg cagcgcaggt     840
agggatagga gatacatctg gaggagtttc agccccaaat gatcattatt gctggatgcg     900
ccctgaggac attgattacc cccgtcctgt atatgaatgt catagttgct ccgatcttgc     960
tgctgaaatg gctgctgctt tggcttcggc ttccatcgtt ttcaaagaca acaaagcata    1020
ctctcaaaag cttgtccatg tgcccgaac actctttaag tttgctaggg atcaaagagg     1080
cagatatagt gctggtcgtt ctgaccctgc cctcttttat aattcctcaa gttactggga    1140
tgagtttgtt tggggtggag cctggttata ctatgccact gggaattcat cctatcttca    1200
gttagctact catcctaaac ttgccaagca tgctggtgct ttctggggtg cccagatta     1260
tggtgttctt agctgggata taagcttgc tggtgctcag gtgcttctga gccgattgag     1320
attgttttg agtcctgggt atccatatga ggaaatattg agtacgtttc ataatcaaac     1380
cagcataatt atgtgctcat tccttccggt tttcactagc tttaatagaa caaaggagg     1440
tttgattcag ttaaaccatg gaaggcctca gccactgcaa tacgtagtca atgcagcctt     1500
cttagccgcc ctatatagtg attatcttga tgctgctgat acacctggat ggtattgtgg    1560
tcccaatttc tattcaactg atgtcctgcg tgaatttgcc aaaacccaga ttgattatat    1620
ccttggcaaa aatcctcgaa aaatgagcta tgttgtgggc tttggtaacc attatccaaa    1680
gcatgttcac catagagggg catctatccc taagaataag atcaaatata actgtaaagg    1740
gggatggaaa tggagggata cgtcaaaacc aaaccccaac acacttgtgg gagccatggt    1800
```

-continued

```
agcaggacct gacaagcatg atgggtttcg tgatgttcgc accaactaca actatacgga    1860
gccaactcta gcaggcaacg cagggttggt tgctgcactc gtggcattgt ctggtgacaa    1920
ggcaaccgtg attgacaaga atactatttt ttctgcagtt ccaccaatgt ttcctacacc    1980
accaccactt ccggcacctt ggaaaccatg aaaacgtttt gatctttctt ctgtccatgt    2040
gtgacttaca gtctgatgat tttggaatta gttttggta cgtaaatgac cttggaagtg     2100
taagtaacgc aaaaaggcaa gacaggagat gagtgatatg agacaacctg acaaaactc     2160 gtggtgtttg gctgtcagat tggagagtca gagaagcatt caaacattga taatttgtat    2220
atgaagtcta tttggatttt gtggtataca gacagacgga gtgcatgtat gatattaatg    2280
ttgtattatt tgaaacacac caatatccat tgacaataaa tttgtgttta attgttgcag    2340
aaatctggcc tttgctatta ccaaaaaaaa aaaaaaaaa ctcgag                    2386
```

<210> SEQ ID NO 6
<211> LENGTH: 783
<212> TYPE: PRT
<213> ORGANISM: Gossypium hirsutum
<220> FEATURE:
<221> NAME/KEY: misc_feature
<223> OTHER INFORMATION: 10 dpa fiber Korrigan homolog from Arabidopsis

<400> SEQUENCE: 6

```
Ala Arg Ala Thr Leu Glu Asn Gln Arg Lys His His Cys Leu Leu Ile
1               5                   10                  15

His Ile Leu Phe Ile Lys Leu Asn Phe Leu Phe Val Leu Val Asp Gln
            20                  25                  30

Ile Cys Arg Cys Ser Cys Ile Phe Arg Pro Leu Leu Phe Gln Ile Leu
        35                  40                  45

Ile Met Tyr Gly Arg Asn Pro Trp Gly Gly Pro Leu Glu Ile Asn Ala
    50                  55                  60

Thr Asp Ser Ala Thr Asp Asp Arg Ser Arg Asn Leu Gln Asp Leu
65                  70                  75                  80

Asp Arg Ala Ala Leu Ser Arg Pro Leu Asp Glu Thr Gln Gln Ser Trp
                85                  90                  95

Leu Leu Gly Pro Gly Glu Gln Lys Lys Lys Lys Tyr Val Asp Leu
            100                 105                 110

Gly Cys Ile Ile Val Ser Arg Lys Ile Phe Val Trp Thr Val Gly Thr
        115                 120                 125

Leu Leu Val Ser Ala Leu Leu Ala Gly Leu Ile Thr Leu Ile Val Lys
    130                 135                 140

Thr Val Pro Arg His His His Arg His Ser Pro Pro Asp Asn Tyr Thr
145                 150                 155                 160

Leu Ala Leu His Lys Ala Leu Met Phe Phe Asn Ala Gln Arg Ser Gly
                165                 170                 175

Lys Leu Pro Lys His Asn Val Ser Trp Arg Gly Asn Ser Gly Leu
            180                 185                 190

Gln Asp Gly Lys Ser Asp Pro Ser Val Leu Met Lys Asp Leu Val Gly
        195                 200                 205

Gly Tyr Tyr Asp Ala Gly Asp Ala Ile Lys Phe Asn Phe Pro Ala Ser
    210                 215                 220

Phe Ser Met Thr Met Leu Ser Trp Ser Val Ile Glu Tyr Ser Ala Lys
225                 230                 235                 240

Tyr Glu Ala Ala Gly Glu Leu Asn His Val Lys Glu Ile Ile Lys Trp
                245                 250                 255
```

-continued

```
Gly Thr Asp Tyr Leu Leu Lys Thr Phe Asn Asn Thr Ala Asp Thr Ile
            260                 265                 270
Asp Arg Ile Ala Ala Gln Val Gly Ile Gly Asp Thr Ser Gly Gly Val
        275                 280                 285
Ser Ala Pro Asn Asp His Tyr Cys Trp Met Arg Pro Glu Asp Ile Asp
        290                 295                 300
Tyr Pro Arg Pro Val Tyr Glu Cys His Ser Cys Ser Asp Leu Ala Ala
305                 310                 315                 320
Glu Met Ala Ala Ala Leu Ala Ser Ala Ser Ile Val Phe Lys Asp Asn
                325                 330                 335
Lys Ala Tyr Ser Gln Lys Leu Val His Gly Ala Arg Thr Leu Phe Lys
            340                 345                 350
Phe Ala Arg Asp Gln Arg Gly Arg Tyr Ser Ala Gly Arg Ser Asp Pro
        355                 360                 365
Ala Leu Phe Tyr Asn Ser Ser Ser Tyr Trp Asp Glu Phe Val Trp Gly
        370                 375                 380
Gly Ala Trp Leu Tyr Tyr Ala Thr Gly Asn Ser Ser Tyr Leu Gln Leu
385                 390                 395                 400
Ala Thr His Pro Lys Leu Ala Lys His Ala Gly Ala Phe Trp Gly Gly
                405                 410                 415
Pro Asp Tyr Gly Val Leu Ser Trp Asp Asn Lys Leu Ala Gly Ala Gln
            420                 425                 430
Val Leu Leu Ser Arg Leu Arg Leu Phe Leu Ser Pro Gly Tyr Pro Tyr
        435                 440                 445
Glu Glu Ile Leu Ser Thr Phe His Asn Gln Thr Ser Ile Ile Met Cys
        450                 455                 460
Ser Phe Leu Pro Val Phe Thr Ser Phe Asn Arg Thr Lys Gly Gly Leu
465                 470                 475                 480
Ile Gln Leu Asn His Gly Arg Pro Gln Pro Leu Gln Tyr Val Val Asn
                485                 490                 495
Ala Ala Phe Leu Ala Ala Leu Tyr Ser Asp Tyr Leu Asp Ala Ala Asp
            500                 505                 510
Thr Pro Gly Trp Tyr Cys Gly Pro Asn Phe Tyr Ser Thr Asp Val Leu
        515                 520                 525
Arg Glu Phe Ala Lys Thr Gln Ile Asp Tyr Ile Leu Gly Lys Asn Pro
        530                 535                 540
Arg Lys Met Ser Tyr Val Val Gly Phe Gly Asn His Tyr Pro Lys His
545                 550                 555                 560
Val His His Arg Gly Ala Ser Ile Pro Lys Asn Lys Ile Lys Tyr Asn
                565                 570                 575
Cys Lys Gly Gly Trp Lys Trp Arg Asp Thr Ser Lys Pro Asn Pro Asn
            580                 585                 590
Thr Leu Val Gly Ala Met Val Ala Gly Pro Asp Lys His Asp Gly Phe
        595                 600                 605
Arg Asp Val Arg Thr Asn Tyr Asn Tyr Thr Glu Pro Thr Leu Ala Gly
        610                 615                 620
Asn Ala Gly Leu Val Ala Ala Leu Val Ala Leu Ser Gly Asp Lys Ala
625                 630                 635                 640
Thr Val Ile Asp Lys Asn Thr Ile Phe Ser Ala Val Pro Pro Met Phe
                645                 650                 655
Pro Thr Pro Pro Pro Leu Pro Ala Pro Trp Lys Pro Lys Arg Phe Asp
            660                 665                 670
```

-continued

```
Leu Ser Ser Val His Val Leu Thr Val Phe Trp Asn Phe Leu Val Arg
        675                 680                 685

Lys Pro Trp Lys Cys Lys Arg Lys Ala Arg Gln Glu Met Ser Asp
    690                 695                 700

Met Arg Gln Pro Gly Gln Asn Ser Trp Cys Leu Ala Val Arg Leu Glu
705                 710                 715                 720

Ser Gln Arg Ser Ile Gln Thr Leu Ile Ile Cys Ile Ser Leu Phe Gly
                725                 730                 735

Phe Cys Gly Ile Gln Thr Asp Gly Val His Val Tyr Cys Cys Ile Ile
            740                 745                 750

Asn Thr Pro Ile Ser Ile Asp Asn Lys Phe Val Phe Asn Cys Cys Arg
        755                 760                 765

Asn Leu Ala Phe Ala Ile Thr Lys Lys Lys Lys Lys Leu Glu
        770                 775                 780
```

<210> SEQ ID NO 7
<211> LENGTH: 1179
<212> TYPE: DNA
<213> ORGANISM: Gossypium hirsutum
<220> FEATURE:
<221> NAME/KEY: misc_feature
<222> LOCATION: (1)..(1179)
<223> OTHER INFORMATION: N is A, C, G, or T

<400> SEQUENCE: 7

```
ctcaaaccac cttgttctcc cccttctcc gtctttctgg caacatgggt tcaccaccac      60
tttgggttct gcttctgggt gtgttgttta tggcttccgg aacaatcgca gctccccta    120
agaagcctgt agatgtacca ttctccagaa actatatgcc tacttgggct tttgatcaca   180
ttaagtattt caatggtggc tctgacattc agctccacct tgacaaatac actggtactg   240
gtttccagtc caaaggatca tacttgttcg dacacttcag tatgcaaata aagctagtcc   300
ctggagattc tgctgggact gtcactgcct gttatttgtc ttctcaaaac tcagagcatg   360
atgagataga ttttgagttc ttgggcaaca gaacagggca accatacatt cttcagacca   420
atgtgttcac tggtggcaaa ggagacagag aacaaaggat ttacctttgg tttgacccaa   480
ccaaagaata ccactcctac tctgtcctct ggaacatgta tcagatantg ttctttgtgg   540
acgacatacc aatcagagtg ttcaaaaact gcaaagattt gggagtgagg tcaaggggtg   600
gtctcgaaaa gaccgactgg tccaaagccc cattcatagc cgcatacaag agcttccaca   660
tcgacgggtg cgagtcgtcg gtggaagcca agttctgcgc cacacaggga aagcggtggt   720
gggaccaaaa ggcattcgag gacctcgacg cctatcagtg gcgcagactg cgttgggtcc   780
gcaacaagtt cactatttac aactattgca gcgatagggt gaggtacccc acaatgtcgc   840
ccgagtgcaa gagagacaga gacgcttgag tcatttccat caccaccgag tcaattgctt   900
gttggccttc acttatttcc acatcaattt cattatatgt aatttcactc ctaaaacatt   960
tgttttcgtg ataatattat ttaaacatag attaccatct cttgacgggg gacaagacca  1020
tnatcttgta agtataagta taagaagctt gggattcgat ttcaagaaat nnaagtctat  1080
ttaaaaaaaa aaaaaaaaa aactcgaggg ggggcccggt acccaattcc gccctatagt  1140
tgagtcctat acnattccac tgggccgtct ttttacaac                         1179
```

<210> SEQ ID NO 8
<211> LENGTH: 274
<212> TYPE: PRT
<213> ORGANISM: Gossypium hirsutum
<220> FEATURE:

```
<221> NAME/KEY: MISC_FEATURE
<222> LOCATION: (162)..(162)
<223> OTHER INFORMATION: X can be any amino acid

<400> SEQUENCE: 8
```

| Met | Gly | Ser | Pro | Pro | Leu | Trp | Val | Leu | Leu | Gly | Val | Leu | Phe | Met |
|---|---|---|---|---|---|---|---|---|---|---|---|---|---|---|
| 1 | | | | 5 | | | | | 10 | | | | | 15 |

| Ala | Ser | Gly | Thr | Ile | Ala | Ala | Pro | Pro | Lys | Lys | Pro | Val | Asp | Val | Pro |
|---|---|---|---|---|---|---|---|---|---|---|---|---|---|---|---|
| | | | 20 | | | | | 25 | | | | | 30 | | |

| Phe | Ser | Arg | Asn | Tyr | Met | Pro | Thr | Trp | Ala | Phe | Asp | His | Ile | Lys | Tyr |
|---|---|---|---|---|---|---|---|---|---|---|---|---|---|---|---|
| | | | 35 | | | | | 40 | | | | | 45 | | |

| Phe | Asn | Gly | Gly | Ser | Asp | Ile | Gln | Leu | His | Leu | Asp | Lys | Tyr | Thr | Gly |
|---|---|---|---|---|---|---|---|---|---|---|---|---|---|---|---|
| | 50 | | | | | 55 | | | | | 60 | | | | |

| Thr | Gly | Phe | Gln | Ser | Lys | Gly | Ser | Tyr | Leu | Phe | Gly | His | Phe | Ser | Met |
|---|---|---|---|---|---|---|---|---|---|---|---|---|---|---|---|
| 65 | | | | | 70 | | | | | 75 | | | | | 80 |

| Gln | Ile | Lys | Leu | Val | Pro | Gly | Asp | Ser | Ala | Gly | Thr | Val | Thr | Ala | Cys |
|---|---|---|---|---|---|---|---|---|---|---|---|---|---|---|---|
| | | | | 85 | | | | | 90 | | | | | 95 | |

| Tyr | Leu | Ser | Ser | Gln | Asn | Ser | Glu | His | Asp | Glu | Ile | Asp | Phe | Glu | Phe |
|---|---|---|---|---|---|---|---|---|---|---|---|---|---|---|---|
| | | | 100 | | | | | 105 | | | | | 110 | | |

| Leu | Gly | Asn | Arg | Thr | Gly | Gln | Pro | Tyr | Ile | Leu | Gln | Thr | Asn | Val | Phe |
|---|---|---|---|---|---|---|---|---|---|---|---|---|---|---|---|
| | | | 115 | | | | | 120 | | | | | 125 | | |

| Thr | Gly | Gly | Lys | Gly | Asp | Arg | Glu | Gln | Arg | Ile | Tyr | Leu | Trp | Phe | Asp |
|---|---|---|---|---|---|---|---|---|---|---|---|---|---|---|---|
| 130 | | | | | 135 | | | | | 140 | | | | | |

| Pro | Thr | Lys | Glu | Tyr | His | Ser | Tyr | Ser | Val | Leu | Trp | Asn | Met | Tyr | Gln |
|---|---|---|---|---|---|---|---|---|---|---|---|---|---|---|---|
| 145 | | | | | 150 | | | | | 155 | | | | | 160 |

| Ile | Xaa | Phe | Phe | Val | Asp | Asp | Ile | Pro | Ile | Arg | Val | Phe | Lys | Asn | Cys |
|---|---|---|---|---|---|---|---|---|---|---|---|---|---|---|---|
| | | | | 165 | | | | | 170 | | | | | 175 | |

| Lys | Asp | Leu | Gly | Val | Arg | Ser | Arg | Gly | Gly | Leu | Glu | Lys | Thr | Asp | Trp |
|---|---|---|---|---|---|---|---|---|---|---|---|---|---|---|---|
| | | | 180 | | | | | 185 | | | | | 190 | | |

| Ser | Lys | Ala | Pro | Phe | Ile | Ala | Ala | Tyr | Lys | Ser | Phe | His | Ile | Asp | Gly |
|---|---|---|---|---|---|---|---|---|---|---|---|---|---|---|---|
| | | | 195 | | | | | 200 | | | | | 205 | | |

| Cys | Glu | Ser | Ser | Val | Glu | Ala | Lys | Phe | Cys | Ala | Thr | Gln | Gly | Lys | Arg |
|---|---|---|---|---|---|---|---|---|---|---|---|---|---|---|---|
| | 210 | | | | | 215 | | | | | 220 | | | | |

| Trp | Trp | Asp | Gln | Lys | Ala | Phe | Glu | Asp | Leu | Asp | Ala | Tyr | Gln | Trp | Arg |
|---|---|---|---|---|---|---|---|---|---|---|---|---|---|---|---|
| 225 | | | | | 230 | | | | | 235 | | | | | 240 |

| Arg | Leu | Arg | Trp | Val | Arg | Asn | Lys | Phe | Thr | Ile | Tyr | Asn | Tyr | Cys | Ser |
|---|---|---|---|---|---|---|---|---|---|---|---|---|---|---|---|
| | | | | 245 | | | | | 250 | | | | | 255 | |

| Asp | Arg | Val | Arg | Tyr | Pro | Thr | Met | Ser | Pro | Glu | Cys | Lys | Arg | Asp | Arg |
|---|---|---|---|---|---|---|---|---|---|---|---|---|---|---|---|
| | | | 260 | | | | | 265 | | | | | 270 | | |

| Asp | Ala |
|---|---|

```
<210> SEQ ID NO 9
<211> LENGTH: 1695
<212> TYPE: DNA
<213> ORGANISM: Artificial Sequence
<220> FEATURE:
<223> OTHER INFORMATION: Consensus PME contig sequence
<220> FEATURE:
<221> NAME/KEY: misc_feature
<222> LOCATION: (1)..(1695)
<223> OTHER INFORMATION: N is A, C, G, or T.

<400> SEQUENCE: 9 aaagctttc   ttggctctct   ttgcgtcaat   ccttcttgta   actgccatag   tcaccattgc    60
caccaccgtc  tccatttcca   aaagaaaatc   cagtaatact   gtagcagctc   actccatcat   120
caaatcttca  tgtagctcca   cgttgtaccc   agagttatgc   tactcaacaa   tctcttcagc   180
```

-continued

```
accagatgct gagaccaagg tcaagaaccc caaggatgtg attgaattgt cgttgaactt       240
gacggtgact gctgttcaga gtaactattt gtccatcaaa aagctcatta gtacccgaag       300
gaagagcctc acggagcgcg aaaaggctgc ccttaacgat tgtcttgaac tagtggatga       360
gactttggat gagctattcg tagctgaaca tgatctcagt gactatccaa gctttaacaa       420
gtcaatttcc caacatgctg atgaccttaa gagtcttctt agtgctgcaa tgaccaacca       480
agaaacttgc cttgatgggt tttctcacga taaagctgat aaaaaggtga ggcaagcgtt       540
gcttgacggg cagatgcatg tttttcatat gtgtagtaat gccctggcaa tgatcaagaa       600
cttgacggac acagacatgg caagccaagg ttatcatcca tcatctggga ggcaacttga       660
ggagcaagac caaacagaat ggcctaaatg gctgtcggag ggagatagga gactgttaca       720
ggctacaaca gtgattccta atgtaacagt ggccgctgat ggtagtggag acttcctcac       780
ggtgtctgag gcggtggcgg ctgcaccgga gagaagcacc acgaggtaca ttattaagat       840
taaagctgga gtttataggg aaacgtggat gtttccaagt aagaaaacca atctcatgtt       900
tgtgggagat gggagggtca acaccatcat cacagctagc agaaatgttg tcgatggcag       960
caccactttc cactctgcca ctgttgctgc ggtaggggac gggttcttgg ccagggatat      1020
aacatttcag aacacggctg gaccatcgaa gcaccaagca gtggcactgc gtgtgggctc      1080
tgatttatca gcattctaca ggtgtggcat tttagcatac caggacactc tctatgtcca      1140
cagccttcgc caattctatt cacaatgcct tgtagcaggc agcgtggact tcatattcgg      1200
aaatgcagca gcagtgttgc aagactgcga cattcatgct cgtcgaccca atccaaacca      1260
aaggaacatg gtcaccgcac aaggncgtag tgacccaaac gagaacactg ggattgtgat      1320
tcanaaatgt nggatcggtg caacctcgga tttagaagcc gttaaatccg attttgaaac      1380
ttatttaggg agaccatgga agacacattc gaagactgtt atcatgcaat ctgttataag      1440
tgatattatt catcctgctg gttggttccc atggggaaaa aaaattcgca ctcnacctttt     1500 gacgtatcng gaatatcana atactnggcc tggancttaa cncntcaanc agggttacat      1560
ggaaaagggt tattacnttta tccccccacat atccggaagc ccaaaaccta cctgcctccg    1620 naattttttnt ttgggggaac ntaattgggt ttancccnc cgggncttnc ctttccctcn      1680
tngaatcttt gaaaa                                                      1695
```

<210> SEQ ID NO 10
<211> LENGTH: 521
<212> TYPE: PRT
<213> ORGANISM: Artificial Sequence
<220> FEATURE:
<223> OTHER INFORMATION: PME consensus sequence
<220> FEATURE:
<221> NAME/KEY: misc_feature
<223> OTHER INFORMATION: Consensus PME contig sequence
<220> FEATURE:
<221> NAME/KEY: MISC_FEATURE
<222> LOCATION: (1)..(9)
<223> OTHER INFORMATION: X can be any amino acid
<220> FEATURE:
<221> NAME/KEY: MISC_FEATURE
<222> LOCATION: (437)..(437)
<223> OTHER INFORMATION: X can be any amino acid
<220> FEATURE:
<221> NAME/KEY: MISC_FEATURE
<222> LOCATION: (450)..(450)
<223> OTHER INFORMATION: X can be any amino acid
<220> FEATURE:
<221> NAME/KEY: MISC_FEATURE
<222> LOCATION: (453)..(453)
<223> OTHER INFORMATION: X can be any amino acid
<220> FEATURE:

```
<221> NAME/KEY: MISC_FEATURE
<222> LOCATION: (507)..(507)
<223> OTHER INFORMATION: X can be any amino acid
<220> FEATURE:
<221> NAME/KEY: MISC_FEATURE
<222> LOCATION: (512)..(512)
<223> OTHER INFORMATION: X can be any amino acid
<220> FEATURE:
<221> NAME/KEY: MISC_FEATURE
<222> LOCATION: (515)..(515)
<223> OTHER INFORMATION: X can be any amino acid
<220> FEATURE:
<221> NAME/KEY: MISC_FEATURE
<222> LOCATION: (518)..(518)
<223> OTHER INFORMATION: X can be any amino acid
<220> FEATURE:
<221> NAME/KEY: MISC_FEATURE
<222> LOCATION: (521)..(521)
<223> OTHER INFORMATION: X can be any amino acid

<400> SEQUENCE: 10
```

```
Xaa Xaa Xaa Xaa Xaa Xaa Xaa Xaa Lys Leu Phe Leu Ala Leu Phe
 1               5                  10                  15
Ala Ser Ile Leu Leu Val Thr Ala Ile Val Thr Ile Ala Thr Thr Val
             20                  25                  30
Ser Ile Ser Lys Lys Lys Ser Ser Asn Thr Val Ala Ala His Ser Ile
         35                  40                  45
Ile Lys Ser Ser Cys Ser Ser Thr Leu Tyr Pro Glu Leu Cys Tyr Ser
     50                  55                  60
Thr Ile Ser Ser Ala Pro Asp Ala Glu Thr Lys Val Lys Asn Pro Lys
 65                  70                  75                  80
Asp Val Ile Glu Leu Ser Leu Asn Leu Thr Val Thr Ala Val Gln Ser
                 85                  90                  95
Asn Tyr Leu Ser Ile Lys Lys Leu Ile Ser Thr Arg Arg Lys Ser Leu
            100                 105                 110
Thr Glu Arg Glu Lys Ala Ala Leu Asn Asp Cys Leu Glu Leu Val Asp
        115                 120                 125
Glu Thr Leu Asp Glu Leu Phe Val Ala Glu His Asp Leu Ser Asp Tyr
    130                 135                 140
Pro Ser Phe Asn Lys Ser Ile Ser Gln His Ala Asp Asp Leu Lys Ser
145                 150                 155                 160
Leu Leu Ser Ala Ala Met Thr Asn Gln Glu Thr Cys Leu Asp Gly Phe
                165                 170                 175
Ser His Asp Lys Ala Asp Lys Lys Val Arg Gln Ala Leu Leu Asp Gly
            180                 185                 190
Gln Met His Val Phe His Met Cys Ser Asn Ala Leu Ala Met Ile Lys
        195                 200                 205
Asn Leu Thr Asp Thr Asp Met Ala Ser Gln Gly Tyr His Pro Ser Ser
    210                 215                 220
Gly Arg Gln Leu Glu Glu Gln Asp Gln Thr Glu Trp Pro Lys Trp Leu
225                 230                 235                 240
Ser Glu Gly Asp Arg Arg Leu Leu Gln Ala Thr Thr Val Ile Pro Asn
                245                 250                 255
Val Thr Val Ala Ala Asp Gly Ser Gly Asp Phe Leu Thr Val Ser Glu
            260                 265                 270
Ala Val Ala Ala Ala Pro Glu Arg Ser Thr Thr Arg Tyr Ile Ile Lys
        275                 280                 285
Ile Lys Ala Gly Val Tyr Arg Glu Thr Trp Met Phe Pro Ser Lys Lys
    290                 295                 300
Thr Asn Leu Met Phe Val Gly Asp Gly Arg Val Asn Thr Ile Ile Thr
305                 310                 315                 320
Ala Ser Arg Asn Val Val Asp Gly Ser Thr Thr Phe His Ser Ala Thr
                325                 330                 335
Val Ala Ala Val Gly Asp Gly Phe Leu Ala Arg Asp Ile Thr Phe Gln
            340                 345                 350
Asn Thr Ala Gly Pro Ser Lys His Gln Ala Val Ala Leu Arg Val Gly
        355                 360                 365
Ser Asp Leu Ser Ala Phe Tyr Arg Cys Gly Ile Leu Ala Tyr Gln Asp
    370                 375                 380
Thr Leu Tyr Val His Ser Leu Arg Gln Phe Tyr Ser Gln Cys Leu Val
385                 390                 395                 400
Ala Gly Ser Val Asp Phe Ile Phe Gly Asn Ala Ala Val Leu Leu Gln
                405                 410                 415
Asp Cys Asp Ile His Ala Arg Arg Pro Asn Pro Asn Gln Arg Asn Met
            420                 425                 430
Val Thr Ala Gln Xaa Arg Ser Asp Pro Asn Glu Asn Thr Gly Ile Val
        435                 440                 445
Ile Xaa Lys Cys Xaa Ile Gly Ala Thr Ser Asp Leu Glu Ala Val Lys
```

```
                    450                 455                 460
        Ser Asp Phe Glu Thr Tyr Leu Gly Arg Pro Trp Lys Thr His Ser Lys
        465                 470                 475                 480
        Thr Val Ile Met Gln Ser Val Ile Ser Asp Ile Ile His Pro Ala Gly
                        485                 490                 495
        Trp Phe Pro Trp Gly Lys Lys Ile Arg Thr Xaa Pro Leu Thr Tyr Xaa
                    500                 505                 510
        Glu Tyr Xaa Asn Thr Xaa Pro Gly Xaa
                515                 520
```

```
<210> SEQ ID NO 11
<211> LENGTH: 20
<212> TYPE: DNA
<213> ORGANISM: Artificial Sequence
<220> FEATURE:
<223> OTHER INFORMATION: COT189 PCR Primer

<400> SEQUENCE: 11
ccatggatct ttgcctggac                                            20

<210> SEQ ID NO 12
<211> LENGTH: 19
<212> TYPE: DNA
<213> ORGANISM: Artificial Sequence
<220> FEATURE:
<223> OTHER INFORMATION: COT185 PCR Primer

<400> SEQUENCE: 12
gcattccagc agcaatacc                                             19

<210> SEQ ID NO 13
<211> LENGTH: 12
<212> TYPE: PRT
<213> ORGANISM: Artificial Sequence
<220> FEATURE:
<223> OTHER INFORMATION: PEPC enzyme glycine-rich motif
<220> FEATURE:
<221> NAME/KEY: MISC_FEATURE
<222> LOCATION: (7)..(8)
<223> OTHER INFORMATION: X is any amino acid

<400> SEQUENCE: 13

Phe His Gly Arg Gly Gly Xaa Xaa Gly Arg Gly Gly
    1               5                   10

<210> SEQ ID NO 14
<211> LENGTH: 10
<212> TYPE: PRT
<213> ORGANISM: Artificial Sequence
<220> FEATURE:
<223> OTHER INFORMATION: PEPC enzyme conserved sequence
<220> FEATURE:
<221> NAME/KEY: MISC_FEATURE
<222> LOCATION: (6)..(6)
<223> OTHER INFORMATION: X us any amino acid
<220> FEATURE:
<221> NAME/KEY: MISC_FEATURE
<222> LOCATION: (9)..(9)
<223> OTHER INFORMATION: X us any amino acid

<400> SEQUENCE: 14

Gly Tyr Ser Asp Ser Xaa Lys Asp Xaa Gly
    1               5                   10

<210> SEQ ID NO 15
<211> LENGTH: 7
<212> TYPE: PRT
<213> ORGANISM: Artificial Sequence
<220> FEATURE:
<223> OTHER INFORMATION: PEPC enzyme motif (residues 168-174)
```

```
<220> FEATURE:
<221> NAME/KEY: MISC_FEATURE
<222> LOCATION: (2)..(2)
<223> OTHER INFORMATION: X is any amino acid

<400> SEQUENCE: 15

Val Xaa Thr Ala His Pro Thr
    1               5

<210> SEQ ID NO 16
<211> LENGTH: 10
<212> TYPE: PRT
<213> ORGANISM: Artificial Sequence
<220> FEATURE:
<223> OTHER INFORMATION: Phosphorylation site-related sequence
<220> FEATURE:
<221> NAME/KEY: MISC_FEATURE
<222> LOCATION: (2)..(3)
<223> OTHER INFORMATION: X is any amino acid

<400> SEQUENCE: 16

Glu Xaa Xaa Ser Ile Asp Ala Gln Leu Arg
    1               5                   10

<210> SEQ ID NO 17
<211> LENGTH: 11
<212> TYPE: PRT
<213> ORGANISM: Artificial Sequence
<220> FEATURE:
<223> OTHER INFORMATION: Phosphorylation site-related sequence
<220> FEATURE:
<221> NAME/KEY: MISC_FEATURE
<222> LOCATION: (3)..(4)
<223> OTHER INFORMATION: X is any amino acid

<400> SEQUENCE: 17

Asp Lys Xaa Xaa Ser Ile Asp Ala Gln Leu Arg
    1               5                   10

<210> SEQ ID NO 18
<211> LENGTH: 10
<212> TYPE: PRT
<213> ORGANISM: Artificial Sequence
<220> FEATURE:
<223> OTHER INFORMATION: Phosphorylation site-related sequence
<220> FEATURE:
<221> NAME/KEY: MISC_FEATURE
<222> LOCATION: (2)..(3)
<223> OTHER INFORMATION: X is any amino acid

<400> SEQUENCE: 18

Arg Xaa Xaa Ser Ile Asp Ala Gln Leu Arg
    1               5                   10

<210> SEQ ID NO 19
<211> LENGTH: 19
<212> TYPE: DNA
<213> ORGANISM: Artificial Sequence
<220> FEATURE:
<223> OTHER INFORMATION: COT285 RT-PCR primer

<400> SEQUENCE: 19
ctttctgcgg agtacgaag                                               19

<210> SEQ ID NO 20
<211> LENGTH: 20
<212> TYPE: DNA
<213> ORGANISM: Artificial Sequence
<220> FEATURE:
```

```
<223> OTHER INFORMATION: COT288 RT-PCR Primer

<400> SEQUENCE: 20
cctgctctca tctcatcttg                                              20

<210> SEQ ID NO 21
<211> LENGTH: 33
<212> TYPE: PRT
<213> ORGANISM: Gossypium hirsutum

<400> SEQUENCE: 21

Val Ile Ser Ile Thr Thr Glu Ser Ile Ala Cys Trp Pro Ser Leu Ile
    1               5                   10                  15
    Ser Thr Ser Ile Ser Leu Tyr Val Ile Ser Leu Leu Lys His Leu Phe
                20                  25                  30
    Ser

<210> SEQ ID NO 22
<211> LENGTH: 18
<212> TYPE: PRT
<213> ORGANISM: Gossypium hirsutum
<220> FEATURE:
<221> NAME/KEY: MISC_FEATURE
<222> LOCATION: (16)..(16)
<223> OTHER INFORMATION: X is any amino acid

<400> SEQUENCE: 22

Tyr Tyr Leu Asn Ile Asp Tyr His Leu Leu Thr Gly Asp Lys Thr Xaa
    1               5                   10                  15
    Ile Leu

<210> SEQ ID NO 23
<211> LENGTH: 31
<212> TYPE: PRT
<213> ORGANISM: Gossypium hirsutum
<220> FEATURE:
<221> NAME/KEY: MISC_FEATURE
<222> LOCATION: (10)..(10)
<223> OTHER INFORMATION: X is any amino acid

<400> SEQUENCE: 23

Glu Ala Trp Asp Ser Ile Ser Arg Asn Xaa Ser Leu Phe Lys Lys Lys
    1               5                   10                  15
    Lys Lys Lys Asn Ser Arg Gly Gly Pro Val Pro Asn Ser Ala Leu
                20                  25                  30

<210> SEQ ID NO 24
<211> LENGTH: 13
<212> TYPE: PRT
<213> ORGANISM: Gossypium hirsutum
<220> FEATURE:
<221> NAME/KEY: MISC_FEATURE
<222> LOCATION: (5)..(5)
<223> OTHER INFORMATION: X is any amino acid

<400> SEQUENCE: 24

Leu Ser Pro Ile Xaa Phe His Trp Ala Val Phe Leu Gln
    1               5                   10

<210> SEQ ID NO 25
<211> LENGTH: 52
<212> TYPE: PRT
<213> ORGANISM: Artificial Sequence
<220> FEATURE:
<223> OTHER INFORMATION: PME consensus sequence fragment
<220> FEATURE:
<221> NAME/KEY: MISC_FEATURE
<223> OTHER INFORMATION: Consensus PME contig sequence fragment
<220> FEATURE:
```

```
<221> NAME/KEY: MISC_FEATURE
<222> LOCATION: (1)..(3)
<223> OTHER INFORMATION: X can be any amino acid
<220> FEATURE:
<221> NAME/KEY: MISC_FEATURE
<222> LOCATION: (13)..(13)
<223> OTHER INFORMATION: X can be any amino acid
<220> FEATURE:
<221> NAME/KEY: MISC_FEATURE
<222> LOCATION: (27)..(27)
<223> OTHER INFORMATION: X can be any amino acid
<220> FEATURE:
<221> NAME/KEY: MISC_FEATURE
<222> LOCATION: (30)..(30)
<223> OTHER INFORMATION: X can be any amino acid
<220> FEATURE:
<221> NAME/KEY: MISC_FEATURE
<222> LOCATION: (34)..(34)
<223> OTHER INFORMATION: X can be any amino acid
<220> FEATURE:
<221> NAME/KEY: MISC_FEATURE
<222> LOCATION: (38)..(38)
<223> OTHER INFORMATION: X can be any amino acid
<220> FEATURE:
<221> NAME/KEY: MISC_FEATURE
<222> LOCATION: (40)..(40)
<223> OTHER INFORMATION: X can be any amino acid
<220> FEATURE:
<221> NAME/KEY: MISC_FEATURE
<222> LOCATION: (42)..(43)
<223> OTHER INFORMATION: X can be any amino acid
<220> FEATURE:
<221> NAME/KEY: MISC_FEATURE
<222> LOCATION: (47)..(48)
<223> OTHER INFORMATION: X can be any amino acid
<220> FEATURE:
<221> NAME/KEY: MISC_FEATURE
<222> LOCATION: (52)..(52)
<223> OTHER INFORMATION: X can be any amino acid

<400> SEQUENCE: 25

Xaa Xaa Xaa Gln Gly Tyr Met Glu Lys Gly Tyr Tyr Xaa Ile Pro His
    1               5                   10                  15
    Ile Ser Gly Ser Pro Lys Pro Thr Cys Leu Xaa Asn Phe Xaa Leu Gly
                    20                  25                  30
    Glu Xaa Asn Trp Val Xaa Pro Xaa Arg Xaa Xaa Pro Phe Pro Xaa Xaa
                35                  40                  45
    Ile Phe Glu Xaa
        50
```